(12) United States Patent
Niehaus

(10) Patent No.: US 7,811,811 B2
(45) Date of Patent: *Oct. 12, 2010

(54) SELF-CONTAINED ASSAY DEVICE FOR RAPID DETECTION OF BIOHAZARDOUS AGENTS

(75) Inventor: Gary D. Niehaus, Kent, OH (US)

(73) Assignee: Northeastern Ohio Universities College of Medicine, Rootstown, OH (US)

(*) Notice: Subject to any disclaimer, the term of this patent is extended or adjusted under 35 U.S.C. 154(b) by 182 days.

This patent is subject to a terminal disclaimer.

(21) Appl. No.: 11/422,828

(22) Filed: Jun. 7, 2006

(65) Prior Publication Data

US 2007/0042489 A1    Feb. 22, 2007

Related U.S. Application Data

(63) Continuation of application No. 10/805,949, filed on Mar. 22, 2004, now Pat. No. 7,060,225.

(60) Provisional application No. 60/456,155, filed on Mar. 20, 2003.

(51) Int. Cl.
    *C12M 1/34* (2006.01)

(52) U.S. Cl. ............... 435/288.7; 422/50; 422/55; 422/61; 422/82.05; 422/82.11; 435/283.1; 435/286.5; 435/287.1; 435/287.2; 435/288.3

(58) Field of Classification Search ........... 422/50, 422/55, 61, 73, 63, 82.05, 82.11; 435/7.1, 435/283.1, 286.5, 287.1, 287.2, 288.3, 288.5, 435/288.7, 291.5, 305.1; 436/501, 518
See application file for complete search history.

(56) References Cited

U.S. PATENT DOCUMENTS 2,645,463 A    7/1953    Stearns et al.

(Continued)

FOREIGN PATENT DOCUMENTS

DE    3617710    7/1987

(Continued)

OTHER PUBLICATIONS

EP 04758032 Supplementary European Search Report, Jun. 12, 2006, Northeastern Ohio Universities College of Medicine.

(Continued)

*Primary Examiner*—Melanie Yu
(74) *Attorney, Agent, or Firm*—Calfee, Halter & Griswold LLP

(57) ABSTRACT

The invention relates to self-contained assay cassette for detecting a ligand in a sample. The assay cassette provides for turbulent flow and mixing of the sample with assay components, including receptors that bind to a ligand, optional microspheres capable of binding the receptors or to which other secondary receptors are attached, and liquid crystalline materials. The assay cassette also provides for laminar flow of the mixed sample into a detection chamber where complexes between a receptor, ligand, and optional microspheres, is detected as transmission of polarized light through the detection chambers. The invention also relates to methods for detecting a ligand in a sample using turbulent flow to mix the sample with assay components, including liquid crystalline materials, and laminar flow of the mixed sample such that the liquid crystalline material assumes an ordered conformation in absence of a ligand.

21 Claims, 17 Drawing Sheets

U.S. PATENT DOCUMENTS

| | | | |
|---|---|---|---|
| 3,306,111 | A | 2/1967 | Ferrin |
| 4,165,644 | A | 8/1979 | Brandt et al. |
| 4,604,364 | A | 8/1986 | Kosak |
| 4,673,657 | A | 6/1987 | Christian |
| 4,794,806 | A | 1/1989 | Nicoli et al. |
| 4,943,525 | A | 7/1990 | Dawson |
| 5,100,626 | A | 3/1992 | Levin |
| 5,116,576 | A | 5/1992 | Stanley |
| 5,149,626 | A | 9/1992 | Fleming |
| 5,447,837 | A | 9/1995 | Urnovitz |
| 5,514,111 | A | 5/1996 | Phelps |
| 5,593,838 | A * | 1/1997 | Zanzucchi et al. ............. 506/5 |
| 5,596,434 | A | 1/1997 | Walba |
| 5,620,252 | A | 4/1997 | Maurer |
| 5,650,327 | A | 7/1997 | Copeland et al. |
| 5,652,149 | A | 7/1997 | Mileaf et al. |
| 5,688,047 | A | 11/1997 | Signer |
| 5,756,696 | A | 5/1998 | Gray et al. |
| 5,780,248 | A | 7/1998 | Milchanoski et al. |
| 5,826,977 | A | 10/1998 | Fowler et al. |
| 5,826,981 | A | 10/1998 | Fowler et al. |
| 5,863,502 | A | 1/1999 | Southgate |
| 5,864,641 | A | 1/1999 | Murphy et al. |
| 5,912,134 | A | 6/1999 | Shartle |
| 6,030,581 | A | 2/2000 | Virtanen |
| 6,043,067 | A | 3/2000 | Lihme |
| 6,062,721 | A | 5/2000 | King et al. |
| 6,171,802 | B1 | 1/2001 | Woolverton et al. |
| 6,284,197 | B1 | 9/2001 | Abbott et al. |
| 6,302,134 | B1 | 10/2001 | Kellogg |
| 6,303,389 | B1 | 10/2001 | Levin et al. |
| 6,319,468 | B1 | 11/2001 | Sheppard, Jr. et al. |
| 6,345,907 | B1 | 2/2002 | Akay |
| 6,361,202 | B1 | 3/2002 | Lee et al. |
| 6,387,328 | B1 | 5/2002 | Berndtsson |
| 6,468,807 | B1 | 10/2002 | Svensson |
| 6,482,328 | B1 | 11/2002 | Davidson et al. |
| 6,813,568 | B2 | 11/2004 | Powell et al. |
| 6,836,326 | B2 | 12/2004 | Hajduk et al. |
| 7,060,225 | B2 | 6/2006 | Niehaus |
| 2002/0052002 | A1 | 5/2002 | Niehaus et al. |
| 2002/0168511 | A1 | 11/2002 | Schneider et al. |
| 2004/0038408 | A1 | 2/2004 | Abbott et al. |
| 2006/0263246 | A1 | 11/2006 | Berndtsson |

FOREIGN PATENT DOCUMENTS

| | | |
|---|---|---|
| WO | 95/33803 | 12/1995 |
| WO | WO 02/079755 | 10/2002 |

OTHER PUBLICATIONS

International Search Report and Written Opinion for PCT/US04/008756, Jun. 14, 2005, Northeastern Ohio Universities College of Medicine.

International Preliminary Report on Patentability for PCT/US04/008756, Sep. 23, 2005, Northeastern Ohio Universities Colege of Medicine.

EP 04758032 Search Report, Mar. 7, 2007, Northeastern Ohio Universities College of Medicine.

Abbott, et al., "Using Liquid Crystals as Probes of Nanostructured Organic Surfaces", (undated) pp. 425-426.

Born, et al., *Principles of Optics*, (1980), Sixth Ed., Pergamon Press, pp. 665-703.

Brooks, et al., "Specificity of Monoclonal Antibodies to Campylobacter Jejuni Lipopolysaccharide Antigens", *Immunological Investigations*, (1998), vol. 27, pp. 257-265.

Buhrer-Sekula, et al., "The Use of Whole Blood in a Dipstick Assay for Detection of Antibodies to Mycobacterium Leprae: A Field Evaluation", *FEMS Immunology and Medical Microbiology*, (1998), vol. 21, pp. 197-201.

Collings, "Liquid Crystals: Nature's Delicate Phase of Matter", 2d Ed., Princeton Science Library (1990), pp. 8-23.

Deng, et al., "Basis for Selection of Improved Carbohydrate-Binding Single-Chain Antibodies from Synthetic Gene Libraries", *Proc. Natl. Acad. Sci. USA*, (1995) vol. 92, pp. 4992-4996.

Grabowska, et al., "Evaluation of Cost-Precision Rations of Different Strategies for ELISA Measurement of Serum Antibody Levels", *J. Immunol. Methods*, (2002), vol. 271, pp. 1-15.

Griffiths, et al., "Human Anti-Self Antibodies with High Specificity from Phage Display Libraries", *The EMBO Journal*, (1993), vol. 12, No. 2, pp. 725-734.

Gupta, et al., "Design of Surfaces for Patterned Alignment of Liquid Crystals on Planar and Curved Substrates", *Science*, (1997), vol. 276, pp. 1533-1536.

Gupta, et al., "Optical Amplification of Ligand-Receptor Binding Using Liquid Crystals" *Science, American Association for the Advancement of Science*, (1998) vol. 279, pp. 2077-2080.

Halfon, et al., "Serological Response to Infection with Different Isolates of Hepatitis C Virus", *Viral Hepat.*, (2002), vol. 9, pp. 438-442.

Harlaw, et al. "Antibodies Laboratory Manual", Cold Spring Harbor Laboratory (1988), Chapter 6, pp. 141-142.

Hartshorne, et al., *Molecular Crystals and Liquid Crystals*, (1973), vol. 23, p. 343, "Mesomorphism in the System Disodium Chromoglycate-Water".

Hasui, et al., *Jpn. J. Appl. Phys.* (2004), vol. 43(4B), pp. 2341-2345, "Low-Birefringence Thermally and Environmentally Stable Slab Waveguide Planarized by Hot Embossing".

Helm, et al., "Measurement of Ligand-Receptor Interactions", *Proceedings of the National Academy of Sciences of the United States*, (1991), vol. 88, pp. 8169-8173.

Hollinger, "Diabodies: Small Bivalent and Bispecific Antibody Fragments", *Proc. Natl. Acad. Sci.*, (1998), vol. 90, pp. 6444-6448.

Jerome, *Rep. Prog. Phys.*, (2001), vol. 54, p. 391-452, "Surface effects and anchoring in liquid crystals".

Jones, "Life in the 21st Century. A Vision for All" *S. Afr. Med. J.*, (1998), vol. 88, Ch. 6, p. 674.

Lee, et al., *Molecular Crystals and Liquid Crystals*, (1983), vol. 91, p. 53, "Phase Diagram and Thermodynamic Properties of Disodium Cromoglycate-Water Lyomesophases".

Lydon, *Current Opin. Colloidal Interface Sci.* (1998), vol. 3, p. 458, "Chromonic liquid crystal phases".

Lydon, "Chromonics", *Handbook of Liquid Crystals*, (1998), vol. 2B, p. 981.

Marks, et al., "By-Passing Immunization Human Antibodies from V-Gene Libraries Displayed on Phage", *J. Mol. Biol.*, (1991), vol. 222, pp. 581-597.

Nannapaneni, et al., Unstable Expression and Thermal Instability of a Species-Specific Cell Surface Epitope Associated with a 66-Kilodalton Antigen Recognized by Monoclonal Antibody EM-7G1 within Serotypes of *Listeria*.

Nastishin, "Brine-Rich Corner of the Phase Diagram of the Ternary System Cteylpyridinium Chloride-Hexanol-Brine", *Langmuir*, (1996), vol. 12, pp. 5011-5015.

Pottiez, et al., Optics, Communications, (2004), vol. 229, pp. 147-159, "Easily tuneable nonlinear optical loop mirror including low-birefringence, highly twisted fibre with invariant output polarisation".

Poulin, et al., *Science*, (1997), vol. 275, p. 1770, "Novel colloidal interactions in anisotropic fluids".

Reinders, et al., "Comparison of the Sensitivity of Manual and Automated Immunomagnetic Separation Methods for Detection of Shiga Toxin-Producing *Escherichia coli* O157:H7 in Milk", *J. Appl. Microbiol.*, (2002), vol. 92, Page.

Sana, et al., "Directed Selection of Recombinant Human Monoclonal Antibodies to Herpes Simplex Virus Glycoproteins from Phage Display Libraries", *Proc. Natl. Acad. Sci. USA*, (1995), vol. 92, pp. 6439-6443.

Schneider, et al., *Langmuir* (2000), vol. 16, p. 5227, "Self-Assebled Monolayers and Multilayered Stacks of Lyotropic Chromonic Liquid Crystalline Dyes with In-Plane Orientational Order".

Seabrook, et al., "Modified Antibodies", (1991) Stockton Press, pp. 53-77.

Sergan, et al., *Liquid Crystals*, (2000), vol. 27, pp. 567-572, "Polarizing-alignment layers for twisted nematic cells".

Sevier, et al., "Monoclonal Antibodies in Clinical Immunology", *Clinical Chemistry*, (1981) vol. 27, No. 11, pp. 1797-1805.

Shinagawa, et al., "Immunoreactivity of a Synthetic Pentadecapeptide Corresponding to the N-Terminal Region of the Scrapie Prion Protein", *J. Gen. Virol.*, (1986), vol. 67, pp. 1745-1750.

Shiyanovskii, et al., "Defects in Liquid Crystals", *Computer Simulations, Theory and Experiments*, (2001), vol. 43, p. 229.

Smalyukh, et al., *Chem. Phys. Lett.* (2001), vol. 336, p. 88, "Three-dimensional imaging of orientational order by fluorescence confocal polarizing microscopy".

Strosberg, et al., "Receptor-Based Assays", *Current Opinion in Biotechnology*, (1991), vol. 2, pp. 30-36.

Sutherland, et al., "Surface Effect Immunoassay", (1991) Stockton Press, pp. 515-542.

Ter Meulen, et al., "Detection of Lassa Virus Antinucleoprotein Immunoglobulin G (IgG) and IgM Antibodies by a Simple Recombinant Immunoblot Assay for Field Use", *J. of Clinical Microbiology*, (1998), vol.

Vasilevskaya, et al., *Russian Chemical Reviews*, (1989), vol. 58, p. 904, "Chromonic Mesophases".

Winter, et al., "Making Antibodies by Phage Display Technology", *Annul. Rev. Immunol.*, (1994), vol. 12, pp. 433-455.

Yamaguchi, et al., *Clin. Chem.*, (2003), vol. 49, p. 275, "Detection of Anti-Human T-Lymphotropic Virus Type I Antibody in Whole Blood by a Novel Counting Immunoassay".

Zamora, et al., "Chemiluminescent Immunoassay in Comparison with the Indirect ELISA as Reference Method for Detecting Salmonella Antibodies in Swine Meat Juice", *Berliner und Munchener Tierarztliche Wochenshritf.*

Shiyanovskii, et al., "Lyotropic chromonic liquid crystals for biological sensing applications", Mol Cryst Liq Cryst, vol. 434, pp. 259/[587]-270/[598], 2005.

European Office Action from European Application No. 04 758 032.9, dated Nov. 29, 2007. 3 pages.

* cited by examiner

Where:
1 = chamber containing antibody
2 = *mixing causway*
2a = baffles designed to induce mixing
3 = chamber containing microspheres
4 = chamber containing liquid crystal
5 = laminar flow causway
6 = detection chamber Where:

1 = syringe barrel
2 = syringe plunger
3 = sample
4 = male leur
5 = female leur
6 = cassette wall
7 = sample expelled into cassette
8 = side ports in valve assembly
9 = valve plug
10 = spring where:
1 = mixing causway
2 = blister pack containing antibody
3 = blister pack wall segment designed to rupture when pressurized
4 = baffel desinged to induce mixing
5 = blister pack containing microspheres
6 = blister pack containing liquid crystal
7 = laminar flow causway
8 = detection chamber

Detection Chamber where:
- 1 = chamber side wall of cassette construction material (foreground wall removed for clarity)
- 2 = transparent plate exhibiting low birefengence
- 3 = plate surface treated to interact with and align liquid crystal with longitudinal axis of chamber (bottom arrow)

where:
1 = light source
2 = director polarizer aligned with the longitudinal axis of the detection chamber
3 = low bifrengence plates whose surface treatment aligns the liquid Crystal with the director orientation
4 = analyser polarizer aligned perpendicular to the longitudinal axis of the chamber
5 = light detector

US 7,811,811 B2

SELF-CONTAINED ASSAY DEVICE FOR RAPID DETECTION OF BIOHAZARDOUS AGENTS

STATEMENT ON FEDERALLY FUNDED RESEARCH

This invention was made with Government support under contract No.: W91CRB04C0016 awarded by Technical Support Working Group. The government has certain rights in this invention.

CROSS REFERENCE TO RELATED APPLICATIONS

This application claims priority to and any other benefit of U.S. patent application Ser. No. 10/805.949, now U.S. Pat. No. 7,060,225 filed Mar. 22, 2004 for SELF-CONTAINED ASSAY DEVICE FOR RAPID DETECTION OF BIOHAZARDOUS AGENTS which claims priority to and any other benefit of U.S. Provisional Application No. 60/456,155, filed Mar. 20, 2004, both of which are incorporated herein by reference in their entirety.

TECHNICAL FIELD OF THE INVENTION

The invention relates to devices and methods for detecting the presence of a ligand in a sample, more specifically for detecting a biohazardous agent in a sample. More particularly, the invention relates to a self-contained cassette comprising a liquid crystal, and methods of using such cassette to analyze test samples. A sample is introduced into the device and tested therein for the presence of a ligand in the sample, wherein interaction and complex formation between the ligand and its receptor is detected. The detection means comprises a liquid crystal matrix which undergoes detectable distortion in its orientational order in the presence of ligand/receptor complex aggregates. The invention also relates to devices that provide the force to move the sample through the assay cassette.

BACKGROUND OF THE INVENTION

Early detection of threat agents can be a great benefit in either disease prophylaxis or therapy before symptoms appear or worsen. Examples of ligand/receptor detection systems for identifying threat agents include, but are not limited to, detection of a pathogenic agent such as a microbe by an antibody, or of a toxin by an antibody, or detection of an antibody in blood by another antibody, or binding of a chemical toxin, such as nerve gas, to its receptor.

U.S. Pat. No. 6,171,802 by Woolverton, Niehaus, Doane, Lavrentovich, Schmidt and Signs, discloses a system for detecting selective binding of a ligand to a receptor and producing an amplified optical signal as the formed receptor-ligand aggregate distorts the orientation of a surrounding liquid crystal matrix (FIG. 1 of this application). The system comprises a receptor (e.g., mono-specific antibody), a ligand (e.g., the specific pathogenic agent that binds to the antibody), and a liquid crystalline material. Under baseline conditions, a uniform nematic liquid crystal slab is positioned between two glass plates whose surfaces are treated to uniformly align the liquid crystal (FIG. 8). The resulting cassette is viewed between two polarizers, a director and an analyzer, with the analyzer oriented 90° out of phase with the director. The easy axis orientation of the liquid crystal matrix (i.e., the direction of positional orientation of the liquid crystal) is aligned with the director and light is projected through the device. Since the analyzer is perpendicular to the polarization of light, light is not transmitted across the uniformly aligned detection system and the cassette appears dark. Under assay conditions, however, the receptor-ligand aggregates, also referred to as inclusion bodies, become embedded in the liquid crystal matrix and induct director distortions in that matrix. The magnitude of director distortion is determined by the balance of the liquid crystal-to-particle anchoring energy versus the elastic energy of director distortions in the liquid crystal bulk. Both anchoring energy and elastic energy are affected by particle size such that individual ligands or receptors are too small to induce detectable distortions, i.e., particle diameter (d) is less than the critical detectable diameter ($d_c$). Larger particles, ligand aggregates for example, that exceed the critical diameter will cause the adjacent liquid crystal to deviate from it's original uniform orientation. The distorted zone will permit light transmission and will appear as an optically detectable bright spot.

U.S. Patent Application Publication No. 2002/0052002, by Niehaus, Woolverton, Lavrentovich, Ishikawa and Doane, discloses an additional system and methods for amplifying receptor-ligand binding to enhance detection signals created in the liquid crystal. The system and method comprise a generally spherical particle capable of binding to the desired ligand. The diameter of the individual spherical particle is less than the critical diameter ($d_c$) and thus does not initiate a detectable optical signal. In one embodiment, the generally spherical particle is coated with a receptor that specifically binds to the ligand (e.g. a microsphere coated with an antibody specific for the ligand; FIGS. 2A and 2B). In another embodiment, the system comprises an antibody specific for the ligand, such antibody not being attached to the generally spherical particle. In this latter embodiment, a generally spherical particle is also provided that is coated with a receptor for the antibody (e.g., a microsphere coated with anti-imununoglobulin). The system also comprises a liquid crystalline material. In the absence of a ligand to which the antibody binds, the liquid crystalline material assumes an ordered orientation (FIG. 3A), and polarized light directed through the system, similar to the description above (FIG. 1A), does not reach a light detector. However, in the presence of a ligand to which the antibody can bind, the microsphere-antibody-ligand complex becomes large enough to exceed the critical diameter, distorts the liquid crystalline material (FIG. 3B), and allows local transmission of light to the photodetector (FIG. 1B). The generally spherical particle thus significantly enhances formation of detectable ($d \gg d_c$) microsphere-antibody-ligand aggregates when ligand concentrations are low.

The systems and methods described in the art do not provide for a self-contained system in which the sample is efficiently mixed with assay components (i.e., receptors and liquid crystalline material) and then analyzed for the presence of complexes between ligand and receptor. There is a need for self-contained systems for rapid and sensitive detection of ligands that can be processed automatically.

SUMMARY OF THE INVENTION

The present invention relates to a self-contained device, called an assay cassette, for rapid, safe, and automatic detection of biohazardous ligands. The cassette comprises one or more mixing chambers configured for mixing various assay components with an introduced sample, such assay components being a receptor (e.g., an antibody) capable of binding to the ligand, an optional generally spherical particle capable of binding to the receptor (e.g., microspheres coated with antibody); and a liquid crystalline material. The device is configured to provide for turbulent flow of the sample and assay components such that there is mixing between the sample and assay components. The device also comprises detection chambers into which the sample that has been mixed with the assay components (i.e., mixed sample) flows. The device is also configured to provide for laminar flow of the mixed sample into the detection chambers such that the liquid crystalline material assumes a uniform alignment with the director except when adjacent to an inclusion body whose diameter exceeds the critical diameter ($d \gg d_c$), e.g., surrounding immune aggregates. The local liquid crystal distortions allow transmission of spots of polarized light through the detection chamber for identification by a photodetector.

The present invention also relates to a device, called a flow device that is in operational communication with the assay cassette. The flow device is programmed to provide a force that moves the sample through the assay cassette and causes mixing of the sample with the assay components. The flow device is also programmed to provide laminar flow of the mixed sample within the detection chamber.

The present invention also relates to a kit comprising an assay cassette and one or more of the following: a system for preparing a sample for introduction into the assay cassette, a flow device, and a device for detecting a signal that is transmitted through the detection chamber of the assay cassette (i.e., a reader device).

The present invention also relates to methods for detecting ligands in a sample. The methods generally comprise introduction of a sample into the cassette, application of a force to move the sample though the cassette, first, such that turbulent flow of the sample and assay components provide mixing of these components and, second, such that flow of the mixed sample into the detection chambers is laminar, for detection of a complex between ligand and receptor.

There are numerous embodiments of the methods and devices described herein, all of which are intended to be non-limiting examples. Additional features and advantages of the invention will be set forth in part in the description which follows, and in part will be obvious from the description, or may be learned by practice of the invention. The features and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention, and together with the description, serve to explain the principles of the invention.

BRIEF DESCRIPTION OF THE FIGURES

While the specification concludes with claims particularly pointing out and distinctly claiming the invention, it is believed that the present invention will be better understood from the following description taken in conjunction with the accompanying drawings in which:

DETAILED DESCRIPTION OF THE INVENTION

Reference will now be made in detail to the present embodiments (exemplary embodiments) of the invention, examples of which are illustrated in the accompanying figures.

Assay Cassettes

The present invention provides for a device that is a closed system for assaying or detecting the presence of a ligand in a sample in a rapid and safe manner. Herein, "closed system" means that after the sample is introduced into the device, the person who is performing the assay, the operator, is not exposed to the sample or any agents within the sample. Such an assay device is called an "assay cassette." The ligand sought to be detected using the cassette is preferably part of, or attached to, a biohazardous agent (e.g., a pathogenic microorganism), or a toxin. The closed system property of the cassette is advantageous because it minimizes contact of the sample with the operator.

Figure 1:
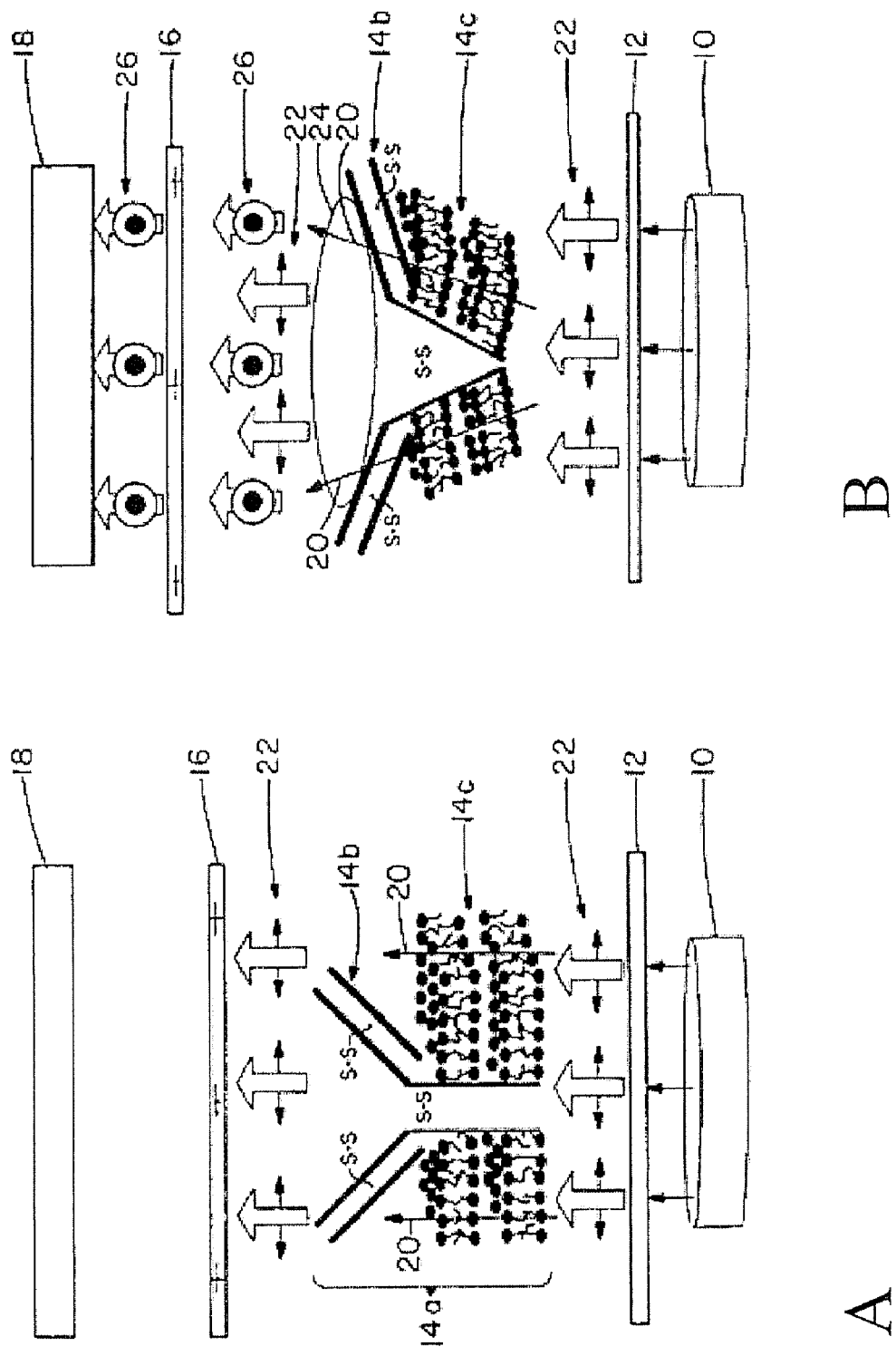
FIG. 1A is a schematic representation of an amplification mechanism with a receptor inserted into the lyotropic liquid crystal. See U.S. Pat. No. 6,171,802.
FIG. 1B is a schematic representation of an amplification mechanism with the specific ligand bound to its receptor causing deformation of the liquid crystal and alteration of the transmission of polarized light. See U.S. Pat. No. 6,171,802.
Figure 2:
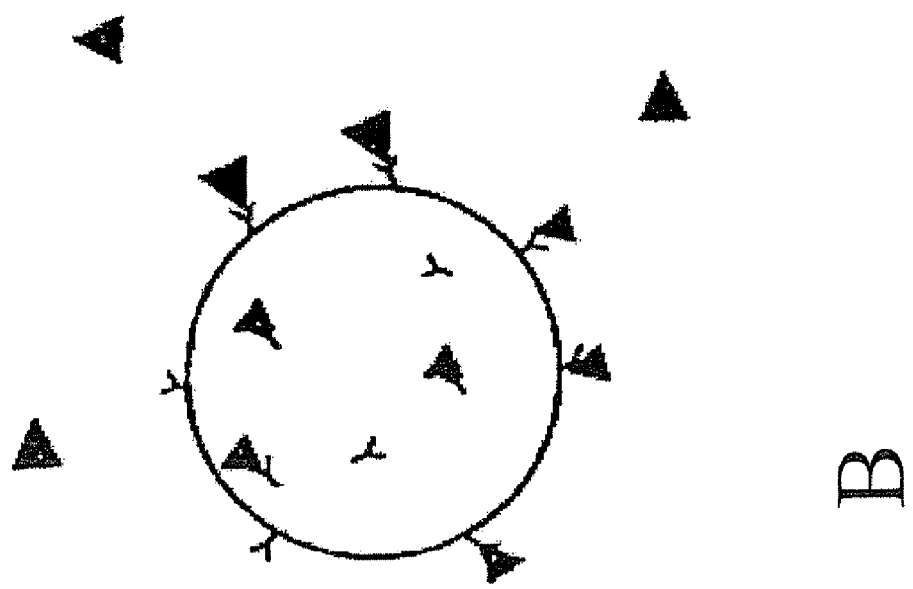
FIG. 2A is a schematic representation of a microsphere having a plurality of receptors (i.e., antibodies) attached to the outer surface of the microsphere. See U.S. Patent Application Publication No. 2002/0052002.
FIG. 2B is a schematic representation of a microsphere having a plurality of receptors attached to the outer surface of the microsphere with ligand bound to a portion of the receptors. See U.S. Patent Application Publication No. 2002/0052002.
Figure 2:
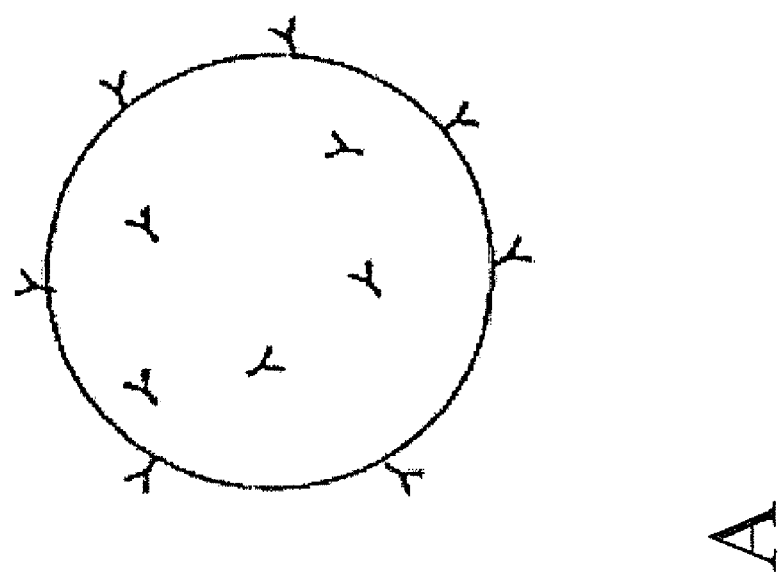
Figure 3:
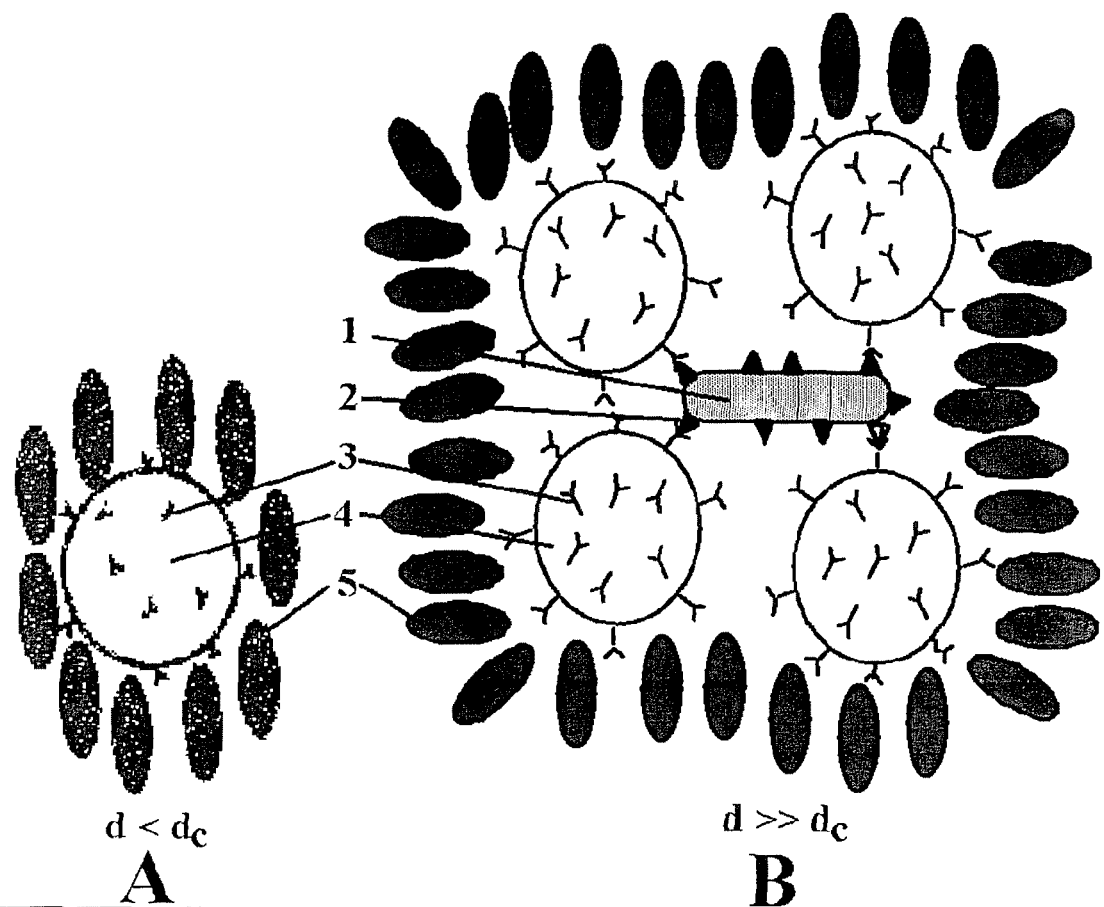
FIG. 3A is a schematic representation of a microsphere having a plurality of receptors (i.e., antibodies) attached to the outer surface of the microsphere showing the liquid crystalline material orientation about the receptor-bound sphere. See U.S. Patent Application Publication No. 2002/0052002.
FIG. 3B is a schematic representation of multiple microspheres having a plurality of receptors attached to the outer surface of the microsphere with ligand of a pathogen bound to a portion of receptors on each microsphere, showing the change in liquid crystalline material orientation about the sphere when ligand is bound.
Figure 4:
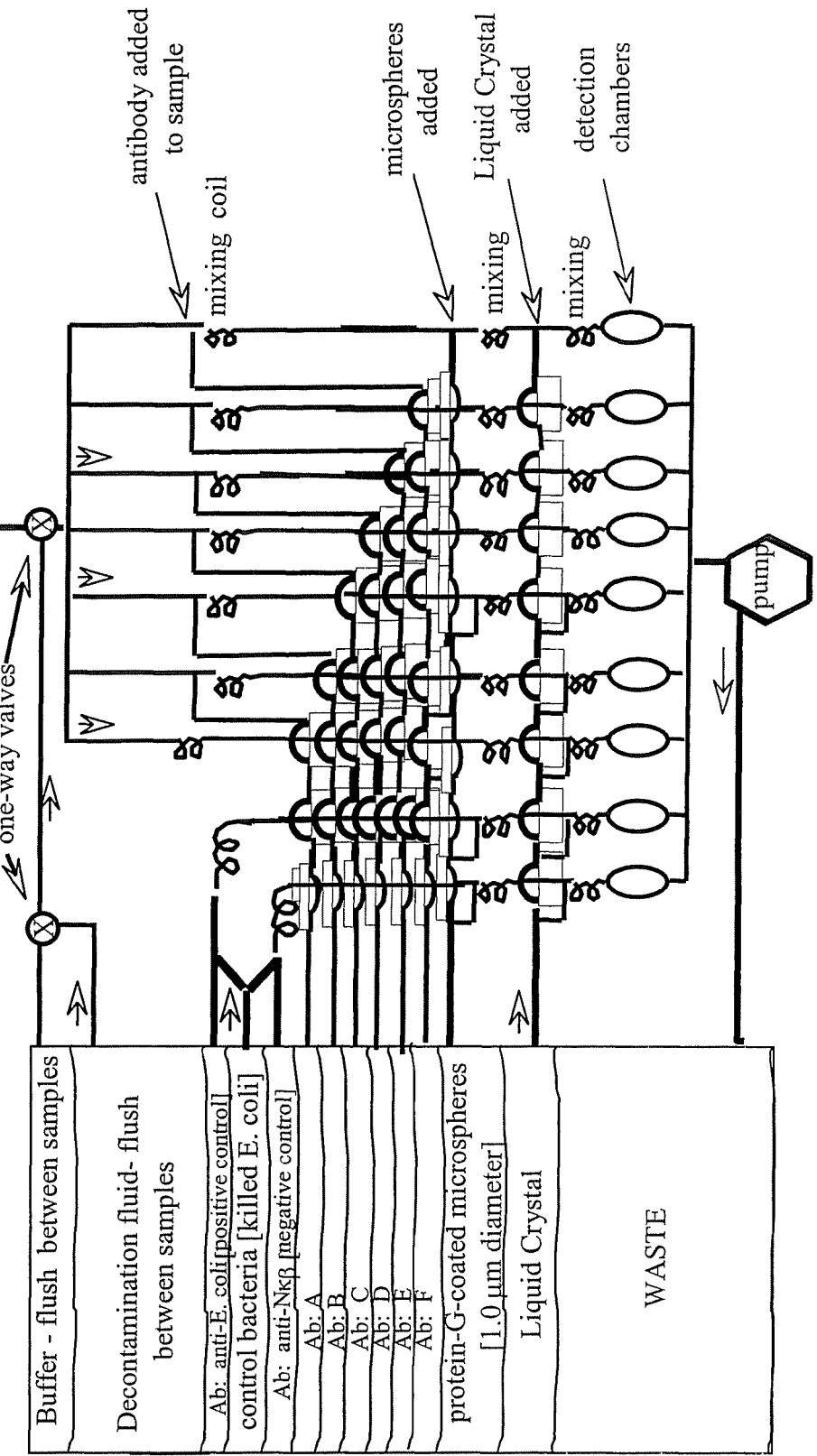
FIG. 4 is a schematic representation of a cassette embodiment for testing a sample for multiple ligands, each tested using a different antibody. This embodiment provides a cassette that can be used to assay several samples before being replaced. A disinfectant is automatically flushed through the cassette between samples. A buffer is also flushed through the lines to remove the disinfectant. The next sample is then introduced into and run through the system. Flow of the sample through this system is provided by a pump.

A highly schematic representation of an assay cassette is shown in FIG. 4. The cassette is generally a linear flow system, such that the introduced sample flows through the cassette and is sequentially mixed with various assay components, such as receptors (i.e., antibodies that specifically bind to the ligand in the sample), generally spherical particles (e.g., microspheres) capable of binding to the antibodies, and liquid crystalline materials. The assay components are preferably enclosed within the assay cassette. In one embodiment, the flow channels are in the form of discrete modules which may be combined in an array, and may optionally be housed in a cassette. The mixing occurs through turbulent flow of the sample and assay components, which flow is provided by the embodiment of the cassette. After the addition and mixing of the assay components with the sample, the design of the assay cassette provides for laminar flow of the mixed sample into a detection chamber. In the presence of ligand/receptor complex aggregates, the orientational order of the liquid crystalline material surrounding the complex is distorted, and allows polarized light to be transmitted through the detection chamber. In the absence of a complex between a ligand and a receptor, the orientational order of the liquid crystalline material is not distorted, and polarized light is not transmitted through the detection chamber.

Figure 5:
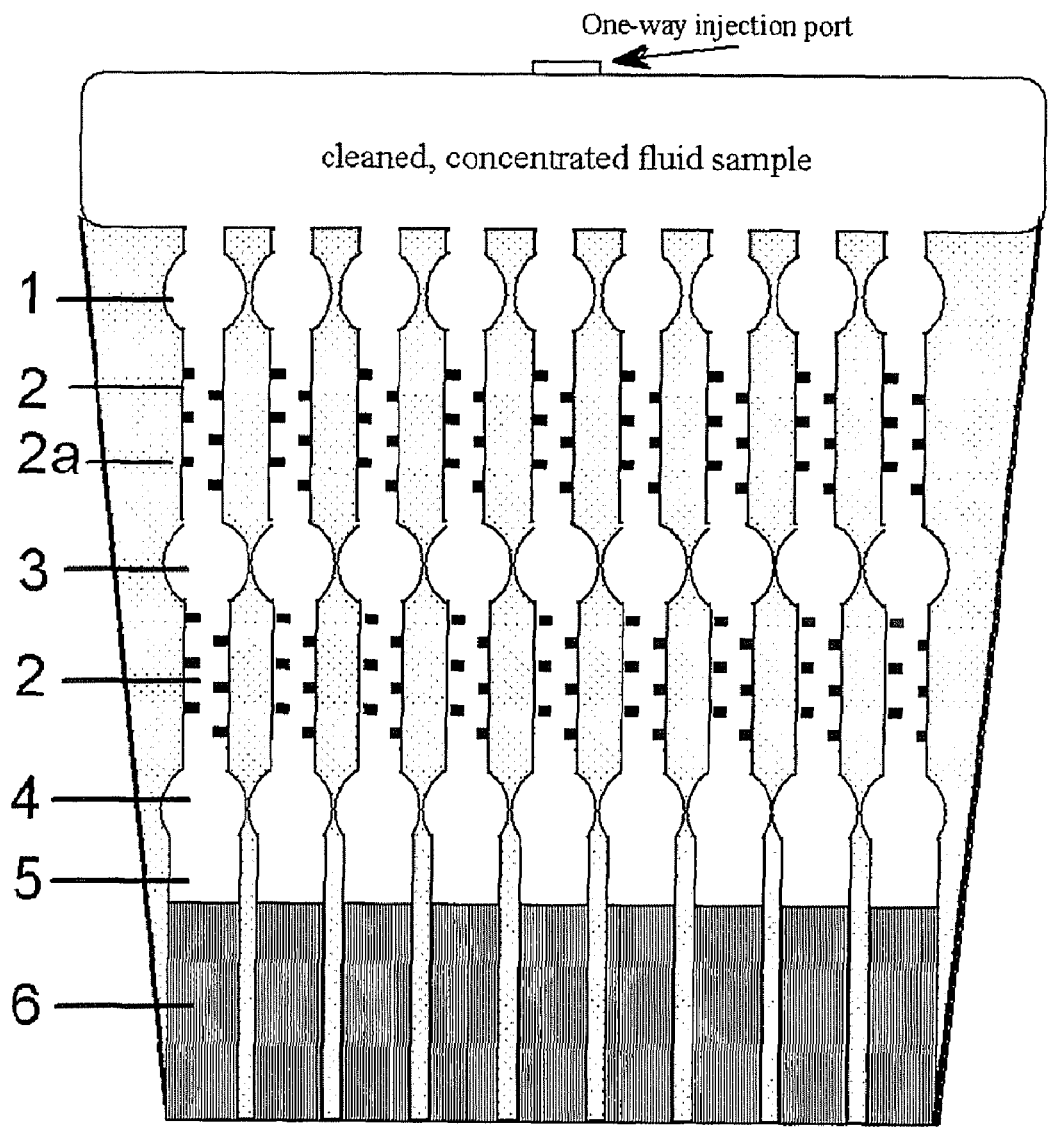
FIG. 5 is a schematic representation of an assay cassette embodiment for testing a sample for the presence of multiple ligands.
Figure 7:
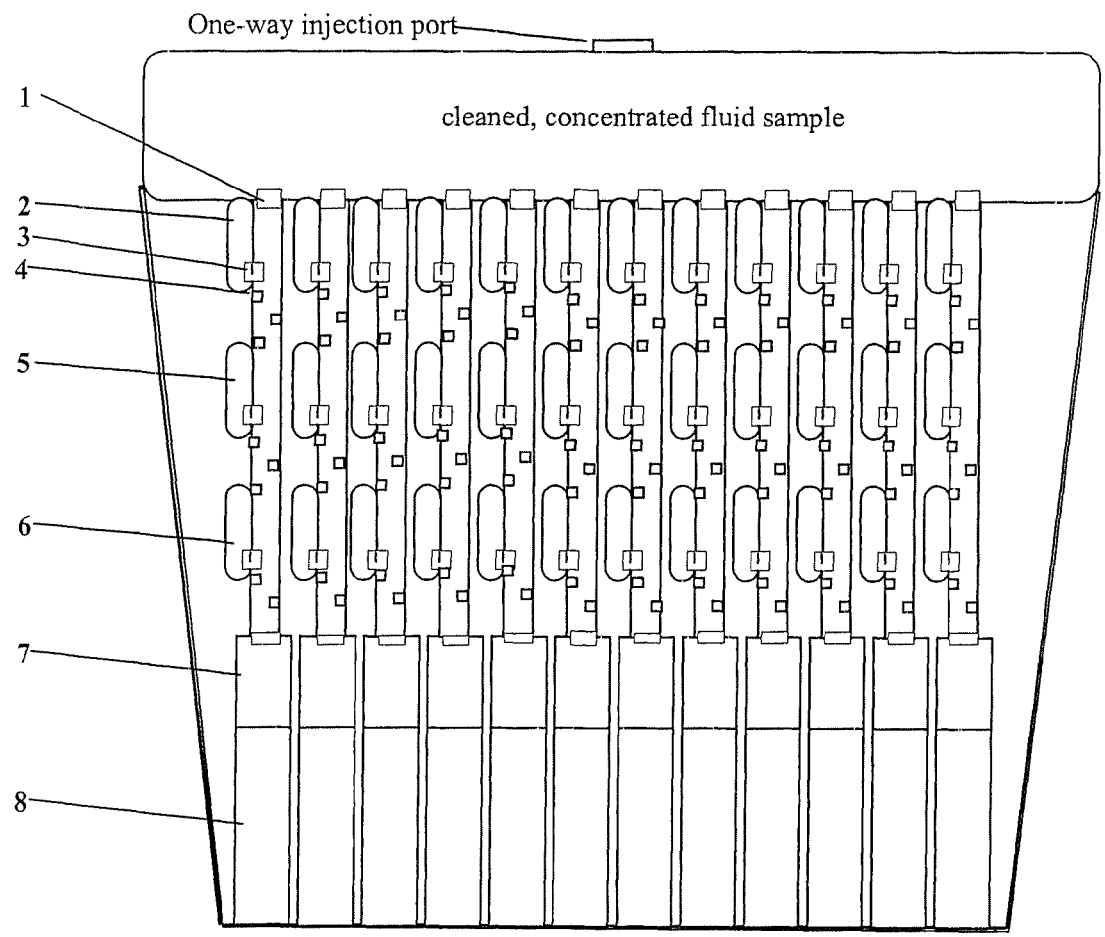
FIG. 7 is a schematic representation of another embodiment for an assay cassette. In this embodiment, assay components are held within holding chambers that comprise blister packs. The blister packs release the assay components as the sample flows through the assay cassette.

In one embodiment, the schematic representation of an assay cassette is as shown in FIG. 5. The cassette shown in FIG. 5 is in the size range of 1 to 6 inches long by 0.5 to 6 inches wide and is preferably in the range less than 0.01 to about 1 inch thinly, and is more preferably less than 0.5 inches thick. In one preferred embodiment, the cassette has a trapezoidal shape. One parallel side of the trapezoid (i.e., the longer of the two parallel sides) is at the top end of the cassette and is the side at which the injection port is located. The shorter parallel side of the trapezoid cassette is located at the bottom end of the cassette and is the side at which the detection chamber is located. The trapezoidal shape of the cassette in this particular embodiment facilitates correct insertion of the assay cassette into the chamber of the flow device, which is discussed later. The assay cassette is made from a material such as plastic or glass. Preferably, the assay cassette (except for the detection chamber) is made from plastic. In one embodiment the assay cassette has an upper and a lower layer. The upper layer can be hard plastic, such as polystyrene. Preferably, the bottom layer is a softer type of plastic, such as polypropylene, or another a type of collapsible plastic (e.g., blister pack material). The collapsible plastic lower layer is attached to the hard plastic top layer in such a way as to form discrete walls and chambers (FIGS. 5 and 7). The detection chamber of the assay cassette comprises on at least two opposing sides low or non birefringent glass.

The assay cassette comprises at least one walled, continuous area interior to the cassette through which a sample is flowable. Optionally, collapsible walls may be located between the chambers to prevent flow there through except when the device is in operation. The assay cassette has a first and a second end. The continuous area begins at a first end of the cassette where a port is located. The port preferably has a one-way valve providing liquid communication between the exterior of the cassette and the continuous area interior to the cassette. As part of the continuous area interior to the cassette, there is at least one mixing chamber in fluid communication with the port. In one embodiment of the assay cassette, a first conduit provides liquid communication between the port and a first mixing chamber, and also provides for turbulent flow of the sample through the conduit. Mixing chambers provide for mixing of the sample with one or more assay components. The mixing chamber preferably provides turbulent flow of the sample and assay components that leads to their mixing. In another embodiment of the assay cassette, there is a second mixing chamber in liquid communication with the first mixing chamber. In this embodiment, a second conduit may provide the liquid communication between the first and second mixing chambers. In still another embodiment of the assay cassette, there is a third mixing chamber in liquid communication with the second mixing chamber. A third conduit may provide the liquid communication between the second and third mixing chambers. The second and third conduits, if present, provide for turbulent flow of the sample through the conduits. The continuous area ends at the second end of the assay cassette where there is a detection chamber in fluid communication, optionally, via a conduit, with the mixing chamber that is nearest the second end of the assay cassette. Depending on the particular embodiment of the assay cassette, the mixing chamber nearest the second end of the cassette may be different. For example, in an assay cassette having one mixing chamber, there is fluid communication between the single mixing chamber (i.e., the first mixing chamber) and the detection chamber. In an assay cassette having two mixing chambers, there is fluid communication between the second mixing chamber and the detection chamber. In an assay cassette having three mixing chambers, there is fluid communication between the third mixing chamber and the detection chamber. The fluid communication between the mixing chamber nearest the second end of the cassette and the detection chamber may be provided by a fourth conduit which provides for laminar flow of the sample and mixed assay components into the detection chamber.

The design of the assay cassette provides for introduction of a fluid sample, turbulent flow of the sample through the cassette in such a way that the sample is mixed with assay components, then laminar flow of the sample mixed with the assay components (i.e., the mixed sample) into a detection chamber of the cassette. This is described in more detail later.

Figure 6:
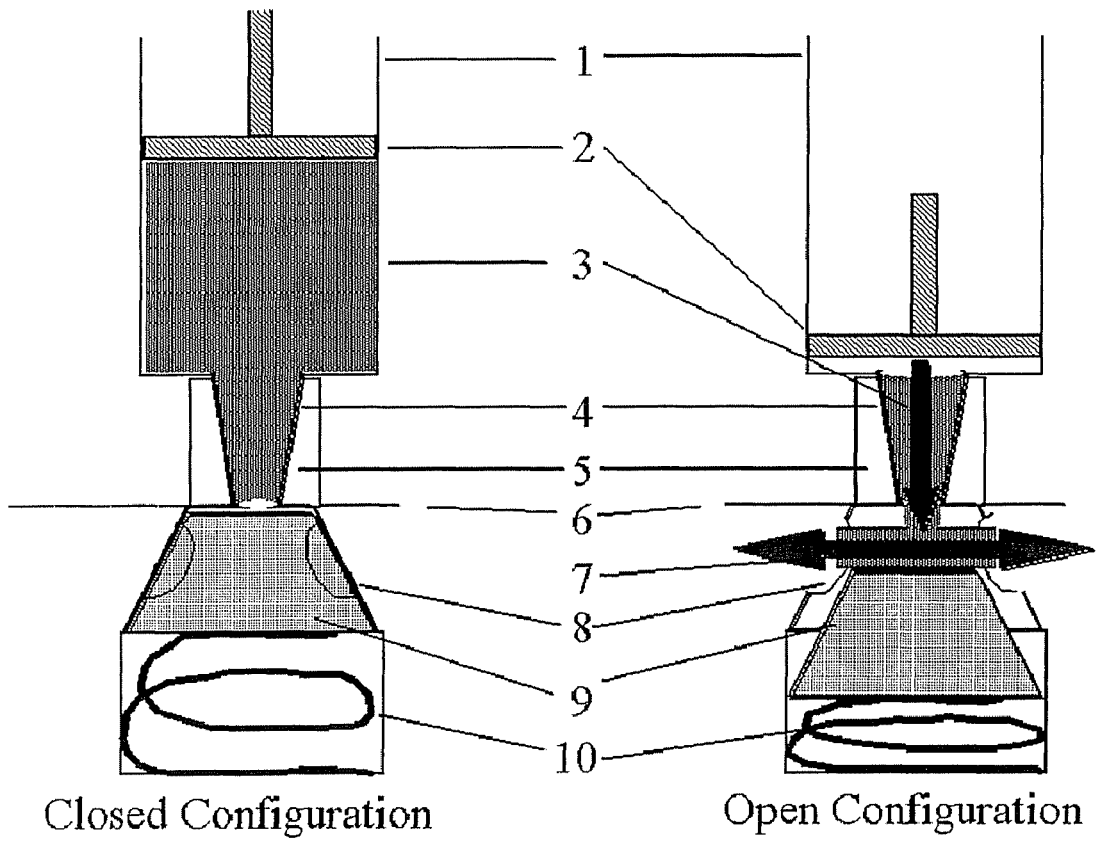
FIG. 6 is an embodiment for an one-way injection valve for the assay cassette.

The sample that is to be tested for the presence of a ligand is introduced into the cassette through a sample or injection port or valve attached the top end of the device. In the particular embodiment shown in FIG. 5, the port is attached to a sample chamber. The port where the sample is introduced into the cassette is of a design such that once the sample is introduced into the device, the sample or its contents do not escape from the cassette and contact with the operator, for example. In one embodiment, the port is a rubber barrier through which a needle attached to a syringe is inserted, and the plunger of the syringe is depressed for the purpose of expelling the sample contained within the syringe into the sample chamber of the assay cassette. Upon removal of the needle from the port, expansion of the rubber to occlude the hole where the needle had been inserted prevents flow of sample out of the cassette. In a second embodiment (FIG. 6), a syringe configured with a male leur-lock end is used to deliver the sample into the chamber. A female leur-lock surrounds the opening to the collection chamber. A spring inside the chamber applies pressure to a tapered plug and causes the plug to occlude the chamber opening. The syringe male leur-lock is inserted into the female leur-lock and rotated to establish a tight seal between the syringe and chamber. The contents of the syringe are pressurized when the plunger of the syringe is depressed. The sample is expelled into the chamber when the hydrostatic pressure in the syringe exceeds the recoil pressure of the spring. The syringe hydrostatic pressure drops as the sample is expelled, and the spring forces the plug back into the sealed configuration. Other designs for one-way ports are possible, and are known in the art.

In one embodiment of the cassette device, the sample is initially introduced into a sample chamber. The sample chamber is a type of holding area for the sample, where the sample is held before subsequent steps are initiated that cause the sample to flow through the device and mix with the various assay components. The sample chamber may also act as an area where the sample is divided into portions for the purpose of contacting each portion of the sample with a separate set of assay components, especially different receptors. Such cassettes that contain multiple receptors are described later.

Mixing Chambers

After introduction into the cassette, the sample flows into mixing areas, called mixing chambers. Mixing chambers are areas in the assay cassette where the sample contacts and mixes with one or more assay components. A mixing chamber comprises at least two walls which define a void, or hollow area, that is generally spherical, elliptical, tubular, or hemispheric in shape. The hollow interior allows two or more fluids to contact each other and be mixed with one another. Generally, the hollow interior defines a void volume large enough to accommodate an increase in volume that occurs when an assay component is added to the sample portion in the assay cassette. As described below, a mixing chamber may have vortex-producing components or structures that induce turbulence to facilitate mixing.

Generally, a single mixing chamber is used to mix a sample portion with each assay component (e.g., antibody, optional microspheres and liquid crystalline material). The embodiment shown in FIG. 5 is such a design where there are separate mixing chambers for mixing the sample with a receptor antibody, microspheres, and liquid crystalline material. Other designs are possible. In another embodiment, a mixing chamber is used to mix more than one assay component with the sample. In one embodiment, a single mixing chamber is used to mix a sample portion with a receptor and microspheres, and a second mixing chamber is used to mix the sample/receptor/microsphere complex with a liquid crystalline material.

Mixing chambers may or may not enclose one or more assay components. In one embodiment, an assay component is held or stored within the mixing chamber (FIG. 5). In one embodiment, there is a compartment within the mixing chamber, such as a blister pack, that holds the assay component and then releases the component to mix with the sample portion as the sample portion flows into the assay chamber. In another embodiment, the assay component added to the sample portion is not enclosed with the mixing chamber per se, but is enclosed within a separate chamber which may be within or outside of the assay cassette, called a holding chamber, for example (FIG. 7). In this embodiment, the assay component is flowed into the mixing chamber from the holding chamber at or before the time when the sample reaches the mixing area. The holding chamber may itself be a blister pack that holds the assay component and then releases the component to mix with the sample portion as the sample portion flows into the mixing chamber. In another embodiment, the assay component is not per se enclosed within the cassette, but is flowed into the mixing chamber from outside the cassette at or before the time at which the sample flows into the particular chamber. The various embodiments of mixing chambers, and/or adjacent conduit sections, provide for turbulent flow to facilitate mixing the sample with the assay components, as described above.

As described earlier, the assay components used in the inventive assay cassette include receptors, such as antibodies, optional microspheres capable of binding to the receptors, and liquid crystalline materials. As described above, there is preferably a separate mixing chamber for each individual assay component. For example, there is a first mixing chamber for mixing of receptor with the sample. There is an optional, separate second mixing chamber for mixing of microspheres with the sample/receptor mix. There is a separate third mixing chamber for mixing of the liquid crystalline material with the sample/receptor/microsphere mix. Each mixing chamber is ordered in the order in which the particular assay component is to contact and mix with the sample. For example, in the case where a receptor is to be mixed with the sample first, microspheres mixed with the sample second, and liquid crystalline material mixed with the sample third, there are three mixing chambers ordered along the length of the path through which the sample flows. In moving from the sample chamber to the detection chamber, the order of the mixing areas along the length of the conduit is the receptor mixing chamber, the microsphere mixing chamber, and the liquid crystalline mixing chamber, respectively. FIG. 5 shows that there is a separate "set" of mixing chambers for each receptor with which the sample, or sample portion, is mixed. In FIG. 5, a "set" of mixing chambers comprises a mixing chamber for mixing of the sample portion with a receptor (designated as "1" in FIG. 5), a second mixing chamber for mixing of the sample portion that has already been mixed with receptor with microspheres (designated as "3" in FIG. 5), then a third mixing chamber for mixing of the sample portion-receptor-microsphere mixture with a liquid crystalline material (designated as "4" in FIG. 5). In other embodiments, a "set" of mixing chambers may comprise a first chamber for mixing the sample portion with receptor and a second chamber for mixing the sample portion-receptor mixture with a liquid crystalline material. As is described below, each set of mixing chambers has a separate detection chamber into which the mixed sample flows for signal detection.

Optionally, there are additional sets of mixing chambers for various positive and negative controls. In one embodiment, for example, there are separate sets of mixing chambers for mixing of a sample portion with different receptors specific for a biohazardous agent. There is an additional set of mixing chambers for a sample portion which is not mixed with a receptor (negative control). There are two additional sets of mixing chambers for mixing a unknown ligand (e.g., E. coli bacterium) with a receptor (e.g., an antibody) known to react with the known ligand (i.e., a positive control) and with a receptor known not to react with the known ligand (i.e., a second negative control).

Detection Chambers

Figure 8:
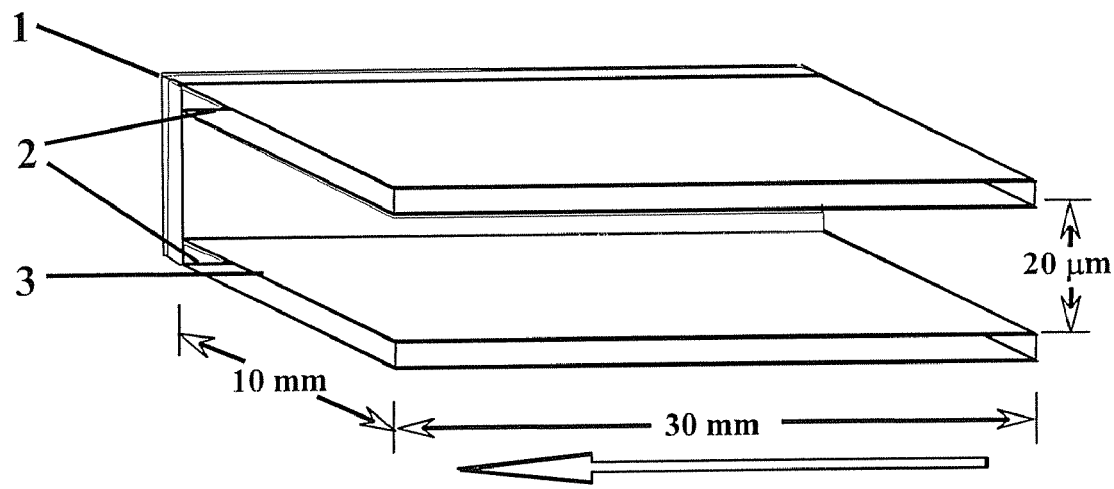
FIG. 8 is a schematic representation of a detection chamber of the assay cassette.

The assay cassette also comprises one or more detection chambers (FIG. 8). There is a separate detection chamber for each set of mixing chambers. The mixed sample portion (i.e., a sample portion which has been mixed with the entire assay components used in the assay) flows into the detection chamber. In a preferred embodiment, the detection chambers are located at the opposite end of the assay cassette relative to where the sample is introduced (i.e., where the sample port is located). In one preferred embodiment, a detection chamber is adjacent to the mixing chamber used for mixing the liquid crystalline material with the sample. The detection chamber is preferably attached to the mixing chamber by a conduit which provides laminar flow of the mixed sample into the detection chamber (discussed below). The detection chamber is constructed of low birefringence glass on at least two opposing walls. In use, polarized light is directed at one wall of low or non birefringent glass and a detector is positioned adjacent to the opposing low or non birefringent glass wall to facilitate detection of light transmitted through the detection chamber. Preferably, the interior surfaces of the opposing low or non birefringent glass walls of the detection chamber (e.g., the base and top of the chamber through which polarized light is directed) are coated with an ~380 nm thick polyimide film which has been surface treated to create parallel, charged microgrooves for facilitating orientational order of the liquid crystalline material (described below). Such microgrooves are parallel to each other and aligned with the flow of the mixed sample into the detection chamber along the axis that is parallel to the direction of flow through the cassette. There are a variety of ways to make such microgrooves. In one method, a laser is used to etch the microgrooves into the surface of the low or non birefringent glass. In another method, the glass is spin-coated with a polyimid, which is normally baked (e.g., 180° C. for 1 hour) onto the interior surface of the glass, and which has been rubbed in the direction of sample flow. In another method, microgrooves are formed by rubbing the surface with a cloth material; good results have been obtained using felt. Formation of microgrooves on the interior surface of the detection chamber, the length of which are in the same direction as the mixed sample flowing into the chamber, facilitate alignment of the liquid crystalline material. The detection chamber preferably holds a volume of the mixed sample that is between 0.05 µl and 100 µl, and more preferably between 5 µl and 25 µl. In one embodiment, the interior of the detection chamber is 30 mm long by 15 mm wide and holds a volume of 15 µl of fluid. In another embodiment, the interior of the detection chamber is 10 mm long by 10 mm wide and holds a volume of ~5 µl of fluid.

In a preferred embodiment, the two walls of the detection chamber through which polarized light is directed, contain light polarizing film attached to the exterior surfaces. The particular side wall closest to the light source has the attached polarizing film aligned with the longitudinal axis of the detection chamber. That is, the polarizing film is attached to the surface of the side wall closest to the light source such that the light, after passing through the first (i.e., director) polarizer, is polarized in the same direction as the microgrooves (along the "easy axis") on the interior surface of the detection chamber; this is also the same direction as the sample flow into the detection chamber). The particular side wall farthest from the light source (and closest to the detector) has the attached polarizing film (i.e., analyzer) aligned perpendicular to the longitudinal axis of the detection chamber.

Connection of Mixing Chambers and Detection Chamber

The assay cassette is designed such that the sample, after introduction into the cassette, flows from one mixing chamber to the next, and then to the detection chamber. In one embodiment of the assay cassette, the separate mixing chambers are located adjacent to one another. In one embodiment, the detection chamber is located adjacent to the last mixing chamber in a set of mixing chambers. In other embodiments, the mixing and detection chambers are not located directly adjacent to one another, but are interconnected by conduits, causeways, channels, tubes or cylinders ("conduits") (designated as "2" in FIG. 5). There may be one conduit positioned between chambers, or a plurality of conduits in series between two chambers. Not all chambers need be connected by conduits, for example, there may be one or more conduits between the inlet port and a mixing chamber, no conduits between two or more mixing chambers, and one conduit between the final mixing chamber and the detection chamber.

The interior areas of conduits are preferably substantially tubular in shape, however they may be elliptical or semi-hemispheric. Conduits may have substantially smooth inner surfaces, or they may comprise structures which influence the flow pattern of fluid moving through the cassette during operation, such that the flow is substantially turbulent. Conduits situated between the final mixing chamber and the detection chamber are preferably smooth on their interior surfaces, and adapted to influence a flow pattern that is substantially laminar when the device is in use. Conduits may have varied internal diameters and dimensions that are either the same as or differ from the internal diameters or dimensions of adjacent conduits or chambers.

The conduits allow the sample portion, and the sample portion mixed with the various assay components, to flow through the assay cassette. In one embodiment, one end of a first conduit is attached to a port which is used for introduction of the sample into the assay cassette. The second end of the first conduit is attached to a first mixing chamber. A second conduit connects the first mixing chamber and a second mixing chamber. A third conduit similarly interconnects the second mixing chamber and, either a third mixing chamber, or a detection chamber. In another embodiment, a sample chamber is attached to a first mixing chamber by a first conduit. A second conduit attaches or interconnects the first mixing chamber to a second mixing chamber. A third conduit interconnects the second mixing chamber to a third mixing chamber. A fourth conduit interconnects the third mixing chamber to a detection chamber. Other embodiments are possible. It is noted that an assay cassette embodiment with multiple sets of mixing chambers and multiple detection chambers, such as the embodiment shown in FIG. 5, is advantageous in that a different receptor or antibody can be reacted with each sample portion. In the case, shown in FIG. 5 for example, a separate portion of the introduced sample is reacted with up to nine receptors. A positive and negative control would each require one detection chamber. If each of the seven remaining antibodies is specific for a different pathogen, for example, the introduced sample is assayed for the presence of seven different pathogens or biohazards. Other cassette embodiments assay for less than seven pathogens or more than seven pathogens.

Chambers and conduits may have gates or valves at their connection interfaces. Such gates or valves operate to prevent the flow of assay components and samples through the system except when in operation. They may also operate to prevent the back flow of assay components and sample mixes toward the first end of the assay cassette when the device is in operation. Gates or valves may be solid structures, the movement or displacement of which may be actuated by various means. In one embodiment, a gate may be a flap that is held in place to prevent the flow of fluid until pressure is applied to the flow path or one or more of the chambers or conduits. Such a flap may be one-way, in that it remains open only when flow is in the direction from the first end of the assay cassette toward the second end, and is closed when the pressure is toward the first end. In another embodiment, a gate or valve may take the form of a soluble membrane which dissolves in the presence of a solvent that is added to the system via the inlet port. An example of such a solvent is water. A variety of gates and valves are known in the art for use in fluid flow systems and devices.

Flow within the Assay Cassette

The assay cassette is configured such that, at or before the point where the sample portion, or a sample portion mixed with one or more assay components, comes in contact with an assay component, there is turbulent flow that provides for mixing of the sample portion with the assay components. Turbulent flow is characterized by the presence of random local circular currents called vortices. In the presence of such vortices, there is transfer of fluid (i.e., mixing) between the solution containing the sample and the solution containing the particular assay component. Turbulent flow can be described through the use of a dimensionless parameter called the "Reynolds number." The Reynolds number is equal to the product of fluid density, the average forward velocity of fluid and the diameter of the conduit through which the fluid flows, divided by fluid viscosity. Generally, a Reynolds number of above approximately 2000 indicates turbulent flow.

There are a variety of methods for creating turbulent flow. The preferred embodiment of the assay cassettes of the present invention uses elements such as moving, or more preferably, non-moving baffles, blades, ribs, bars, and the like, present within mixing chambers or conduits that generally disrupt the flow of the sample portion and assay components by causing shearing, swirling or change of direction of the sample portion and assay components, for example (designated as "2a" in FIG. 5). Such elements are called vortex-producing elements. These elements are placed in the path of the flowing fluid, by locating the elements inside the conduits and/or mixing chambers. Through the use and placement of these elements, the cassette design provides for either or both of: i) turbulent flow of the sample and the assay component, and subsequent contacting of the turbulently flowing sample and assay component that results in mixing, and ii) contacting of the sample and assay component and production of subsequent turbulent flow that results in mixing of the sample and assay components.

There are devices known in the art as "static mixers" which provide a variety of ways for mixing different components, such as different fluids or fluid mixtures, together to form a homogeneous mass. Such additional method known in the art of static mixers can be used to provide the turbulent flow of the inventive assay cassettes.

One way to determine whether the design of the assay cassette provides turbulent flow sufficient for mixing of sample and assay components in the assay cassette is determined by adding a number of microbeads (1-2 µm) to the sample that is introduced into the cassette or to a given assay component that is introduced into the system. The microbeads provide a visual marker to what happens to the particular fluid, whether sample or assay component. Mixing of the microbeads is visualized, with or without use of a low-power microscope, as the sample flows through the cassette. In the case where the design of the particular assay cassette provides turbulent flow sufficient for mixing, visual observation of an operating assay cassette shows complete dispersement of the microbeads from the fluid in which the microbeads are originally present into the fluid that is being mixed with the fluid containing the microbeads.

The assay cassette is also configured such that, after all assay components have been mixed with the sample or sample portion, there is laminar flow of the mixed sample. Components of the assay cassette that provide laminar flow, therefore, are preferably present in the cassette as the mixed sample leaves the final mixing chamber, e.g. the one that mixes liquid crystalline material with the sample (see component "5" in FIG. 5). The laminar flow facilitates formation of the liquid crystalline material into an ordered arrangement after flow of the mixed sample into the detection chamber of the assay cassette. In contrast to turbulent flow, as described above, in laminar flow, the fluid flows in smooth layers or lamina. This occurs when adjacent fluid layers slide smoothly over one another with little mixing between layers. Vortices are not present. Generally, a Reynolds number of below approximately 2000 indicates laminar flow.

One preferred method of creating laminar flow in the inventive assay cassette is to provide a length of conduit, located between the detection chamber and the nearest mixing chamber, that is of a greater internal diameter than is the conduit present earlier in the flow path of the assay cassette (see component "5" in FIG. 5). This conduit has no vortex-producing components. The effect of the larger diameter conduit, with no vortex-producing components, is to slow velocity of the flow of the mixed sample through the system, thus lessening and, preferably eliminating the turbulent flow established earlier in the system. Providing laminar flow before and as the mixed sample enters into the detection chamber provides for the liquid crystalline material, in absence of a ligand in the sample, to assume an ordered arrangement in the detection chamber in a minimal amount of time (i.e., preferably less than 30 minutes). An ordered arrangement of the liquid crystalline material can be visually observed.

In addition to the embodiment shown in FIG. 5, other embodiments of the assay cassette are possible. Cassettes are preferably designed for single use and then to be disposed of. The cassettes may be designed such that they contain different sets of mixing chambers and detection chambers. That is, a cassette may have a single set of mixing chambers/detection chambers. Such a cassette is useful for determining whether a single, specific ligand is present in a sample. Other cassette designs may have multiple sets of mixing chambers/detection chambers, each set useful for determining the presence of a single ligand in the sample. Because such cassettes are able to test a sample for the presence of multiple ligands in the sample, they can efficiently test a sample for one of a number of ligands in a single assay. It is also possible that a sample contains multiple ligands. Such cassettes having multiple mixing chambers/detection chambers are useful for detecting and determining the identity of such ligands in a single assay.

Flow and Reader Devices

In order for the sample to flow through the assay cassette, a force is provided. The force providing for flow of the sample through the assay cassette device is preferably provided by a flow device located outside of the self-contained cassette. The flow device provides that the sample movement through the assay cassette is automatic, meaning that once flow of the sample through the cassette is initiated, the operator need no longer monitor or control the process. In one embodiment, the flow devices have a compartment into which the assay cassette is inserted Preferably, the compartment is shaped in such a way that the assay cassette (e.g., the trapezoidal shape in FIG. 5) fits into the compartment in only one orientation. Such flow devices can provide this force in a variety of ways. In one embodiment, the flow device is an external pump that moves the sample through the device. In another embodiment, which is preferred when the assay cassette is of a collapsible design, the flow device is a roller that contacts one end of the assay cassette (i.e., the end containing the introduced sample) and then rolls over the length of the cassette, compressing the cassette as it goes, providing pressure that flows the sample along the length of the cassette, and then stopping rolling movement when the mixed sample has flowed into the detection chamber.

Figure 10:
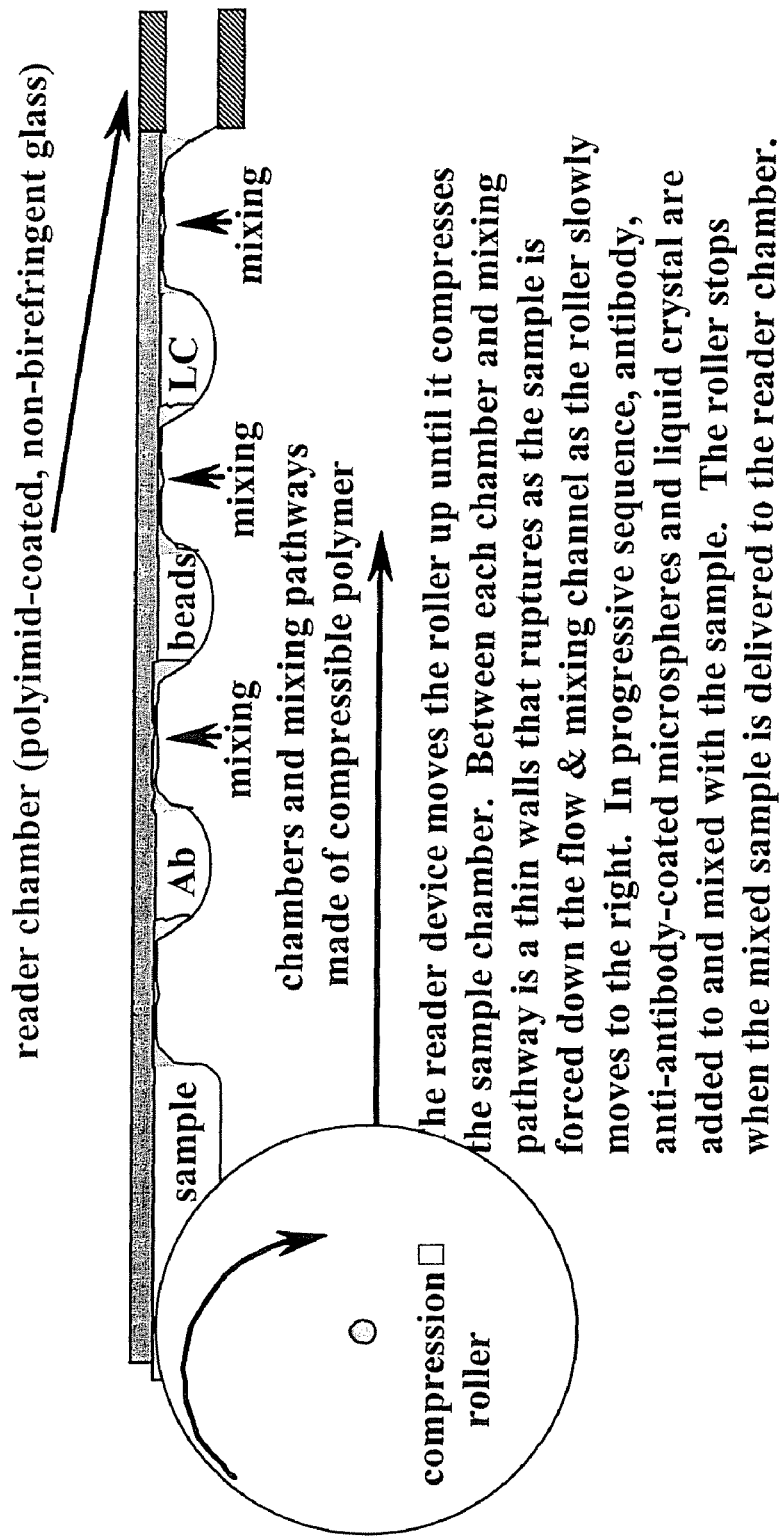
FIG. 10 is a schematic representation of one embodiment of a roller device, here being used with a collapsible blister pack assay cassette.
Figure 11:
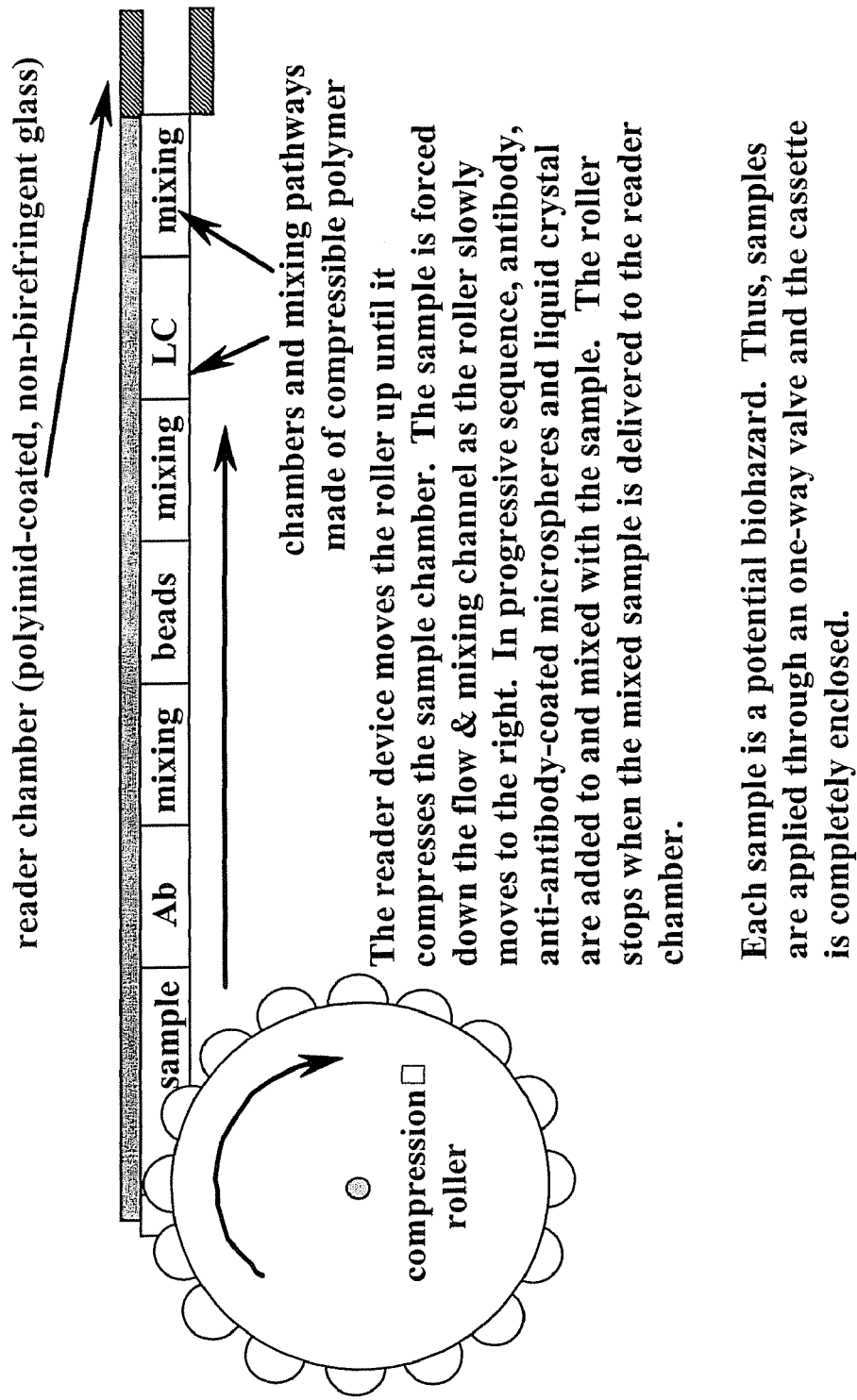
FIG. 11 is a schematic representation of another embodiment of a roller device.

One such roller device is shown in FIG. 10, functioning to move a sample through a collapsible assay cassette of the blister pack type, preferably as illustrated in FIG. 5. Another such roller device is shown in FIG. 11, functioning to move a sample through a collapsible assay cassette. The roller device illustrated in FIG. 10 moves the roller up until it compresses the sample chamber. On both sides of each mixing chamber of the cassette (FIG. 5) are thin collapsible walls that rupture as the sample is flowed down the conduit by advancement of the roller. Rupture of the walls releases the assay component contained within the mixing chamber and the assay component then mixes with the sample. The roller stops when the mixed sample is flowed into the detection chamber.

The roller device illustrated in FIG. 11 is similar to the device shown in FIG. 10 except that the compression roller is of a different design. The multiple round surfaces on the surface of this particular compression roller are useful to provide a peristaltic type of sample flow. Like the earlier roller device, this device moves the roller up until it compresses the sample chamber. The sample is forced down the conduit as the roller slowly moves to the right. In progressive sequence, antibody, anti-antibody-coated microspheres and liquid crystal are added to and mixed with the sample. The roller stops when the mixed sample is delivered to the detection chamber.

Whatever force or device is used to provide for flow of the sample through the cassette, the device must provide flow that results in mixing of the sample with the various assay components. That is, as described earlier, the sample flow at the point where mixing occurs is preferably turbulent. In addition, the force preferably moves the sample at a slow enough rate through the cassette to permit adequate levels of mixing. In addition, the force used to provide for flow of the sample through the cassette must also provide for lack of turbulence (i.e., laminar flow) at and before the point where the mixed sample enters the detection chamber of the cassette device. As described earlier, laminar flow can be provided by increasing the interior diameter of the length of conduit that connects to the detection chamber. Another way of providing the laminar flow is to decrease the flow rate of the sample as it approaches the detection chamber. Using the roller devices shown in FIGS. 10 and 11, for example, the decrease in sample flow rate is provided by slowing the rate at which the roller advances along the assay cassette. The lack of turbulence facilitates the liquid crystalline material in forming an ordered arrangement (i.e. no distortion) in the detection chamber in the absence of a ligand-antibody complex.

The roller device and its motion is preferably controlled by an instruction set, at least part of which has been pre-determined. For example, the program can be in the form of a microchip that contains instructions for directing the motion of the compression roller of the device in order to move or flow a sample through the assay cassette. In one embodiment, at least some instructions of the program can be modified by the user based, for example, on the particular assay cassette that is being used, the force desired, and so forth. Some of the parameters of the roller device controlled by the program may be: the speed at which the compression roller moves along the assay cassette; changes in the speed during the run such as those changes providing turbulent flow and laminar flow; the force applied to the cassette and changes in the applied force; the position at which the compression rollers stop their motion along the cassette; the particular cassette type and/or size which is to be used in the roller device; and other such parameters of the roller's movement.

Such a pre-programmed flow device, such as a pre-programmed roller device, provides for flow of a sample through an assay cassette in such a way that the sample or sample portion turbulently flows such that the sample portion is mixed with assay components, and also provides for laminar flow of the mixed sample into the detection chamber of the assay cassette. The device may also provide for monitoring of various parameters of sample flow through the cassette and, based on the monitoring, adjustment of various motions of the roller device based on the measured parameters. These pre-programming and feedback features of the device allow for minimal input from the operator in order to perform the assay and provides consistent, valid results.

In addition to a device that provides a force that moves the sample through the assay cassette, a reader device is provided. The reader device provides the light source, and light detectors (e.g., photodiodes) used to determine if a ligand bound to its receptor is present in the detection chamber of the assay cassette. The reader device may also provide the two light polarizers. The reader device can be a device separate from the flow device. The reader device may also be incorporated into the flow device so a single unit both provides the force moving the sample through the assay cassette and also determines whether a ligand from the sample binds its receptor and is present in the detection chamber of the assay cassette.

Assay Components

Assay components comprise receptors for ligands (preferably antibodies), optional generally spherical particles (preferably microspheres), and liquid crystalline material.

Receptors

The receptors for ligands are capable of binding a specific ligand whose presence in a sample is sought to be determined. Receptors include but are not limited to proteins, such as specific biological receptors, antibodies or antibody fragments, peptides, bio- and non-biopolymers, fatty acids, oligonucleotides such as DNA and RNA, natural and synthetic macromolecules and other molecules which are specific for and bind or interact with specific ligands. Examples of receptors include enzymes that recognize substrates and inhibitors; antibodies that bind antigens, antigens that recognize target antibodies, receptors that bind ligands, ligands that bind receptors, nucleic acid single-strand polymers that can bind to form DNA-DNA, RNA-RNA, or DNA-RNA double strands, and synthetic molecules that interact with targeted ligands.

Receptors may be prepared using a variety of known techniques, including macromolecule synthesis, recombinant gene expression of biological macromolecules, antibody production and phage display. Phage display is a commonly used method for displaying a high number of macromolecules such as peptides and proteins, including human antibodies and enzymes, on the surface of a small bacterial virus called a phage. This method permits screening of a large number of potential ligands in order to identify those compounds that bind with high affinity and high specificity to the phage-bound molecules. Using the phage display process, receptors which are specific for target analytes, specifically known threat agents, are identified by generating one or more phage libraries which express the target analyte on the phage surface, screening the phage display libraries to select binding compounds with high affinity and high specificity to the target analyte, and producing and evaluating the selected binding compounds. Phage display can be used in combination with one or more of the known methods for making receptors in order to select and confirm the most specific reagents which have the highest affinity for the target analyte.

Antibody reagents for detection of many pathogens of interest are commercially available, or can be conveniently produced from available hybridomas. Additionally, specific antibody or peptide receptors can be produced de novo using phage display or other protein engineering and expression technologies.

In a preferred embodiment, receptors are antibodies. Antibodies can be monoclonal antibodies, polyclonal antibodies, or even phage-displayed mono-specific antibodies. The antibodies preferably specifically bind to or are immunospecific for ligands that are part of, or attached to, a pathogenic agent or a toxin, for example.

The antibodies may or may not be attached to the surface of generally spherical particles, another optional assay component. If they are attached, the antibodies may be attached to the generally spherical particles in any manner known in the art, including chemical attachment and physical attachment. In one preferred embodiment, the receptors are attached to the spherical substrate by a chemical attachment, such as by covalent bonding to sulfate, amine, carboxyl or hydroxyl groups imbedded in the spherical substrate.

If the antibodies are not attached to the generally spherical particles and generally spherical particles are used, then other receptors are present on the surface of the generally spherical particles, such receptors having the capability of binding to the antibodies that are not attached to the surface of the particles. Such receptors are anti-immunoglobulins, for example.

Generally Spherical Particles

The spherical particles are made from a material including, but not limited to, polymeric and inorganic materials. In one preferred embodiment, the substantially receptor-coated spherical substrate is comprised of a polymeric material. Suitable polymeric materials which may comprise the spherical substrate include, but are not limited to, polyalkenes, polyacrylates, polymethacrylates, polyvinyls, polystyrenes, polycarbonates, polyesters, polyurethanes, polyamides, polyimides, polysulfones, polysiloxanes, polysilanes, polyethers, polycations, polyanions, and polycarboxylates. One particularly useful polymeric material used to manufacture the spherical substrate is polystyrene, especially when modified with copolymers of acrylic ester, chloromethylstyrene, methylolamine, methyl methacrylate or made zwitterionic. If a polycation is utilized as the material of the spherical substrate, one particularly suitable polycation is poly (diallyldimethylammoniumchloride). In another embodiment, the substantially receptor-coated spherical substrate is made from an inorganic material. Suitable inorganic materials include, but are not limited to, glass, silicon, and colloidal gold. In one preferred embodiment, the spherical substrate is a glass bead. The spherical particles are preferably microspheres. The spherical particles are preferably <1 µm in diameter.

Liquid Crystalline Material

Another assay component is liquid crystalline material. Liquid crystalline material is a material capable of forming a state of matter in which molecules exhibit some orientational order (i.e., individual liquid crystalline molecules assume an ordered arrangement with respect to each other) but little positional order (i.e., the location of individual liquid crystalline molecules is not fixed). This property of intermediate ordering means that liquid crystals are neither solids (which possess both orientational and positional order) nor isotropic fluids (which exhibit no long-range order), but rather have properties between the two. Solid crystal or isotropic fluid can be caused to transition into a liquid crystal by changing temperature (creating a thermotropic liquid crystal) or by using an appropriate diluting solvent to change the concentration of solid crystal (creating a lyotropic liquid crystal). In the present invention, the liquid crystalline material is used to produce and amplify a light signal due to the presence of ligand-receptor complexes.

A variety of types of liquid crystals can be used in the assay cassettes as long as the liquid crystalline material does not dissolve or other wise affect the ability of the ligand in the sample to bind and form a complex with receptors. Surfactant lyotropic liquid crystals and thermotropic liquid crystals, therefore, are less preferable because these can dissolve ligands and/or receptors due to surfactant properties or temperature.

The liquid crystalline material preferred for use in the assay cassette includes lyotropic chromonic liquid crystalline material (LCLC) is used as the liquid crystalline material in the device of the present invention. The LCLC family embraces a range of dyes, drugs, nucleic acids, antibiotics, carcinogens, and anti-cancer agents. For a review of lyotropic chromonic liquid crystals see J. Lydon, Chromonics, in: Handbook of Liquid Crystals, Wiley-VCH, Weinheim, vol. 2B, p. 981 (1998). Cromolyn is one LCLC that can be used in the assay cassettes of the present invention.

The Assay

The basis for the assay is that insertion of inclusion bodies in the bulk of a liquid crystal matrix drastically alters the optical properties of the liquid crystalline medium (i.e., detectable birefringence is produced by the foreign bodies). More specifically, the orientational order of the LCLC used in the cassettes is opaque to polarized light. The assay system is designed so that local orientational order of the liquid crystal is disrupted or distorted (i.e., the optical anisotropy is destroyed) by a ligand binding to its specific receptor. In this distorted state, at least some polarized light passes through the liquid crystal. It is detection of this transmitted light that is the basis for detecting the presence of a ligand in a sample. The LCLC is used to detect and amplify this polarized light signal.

Figure 9:
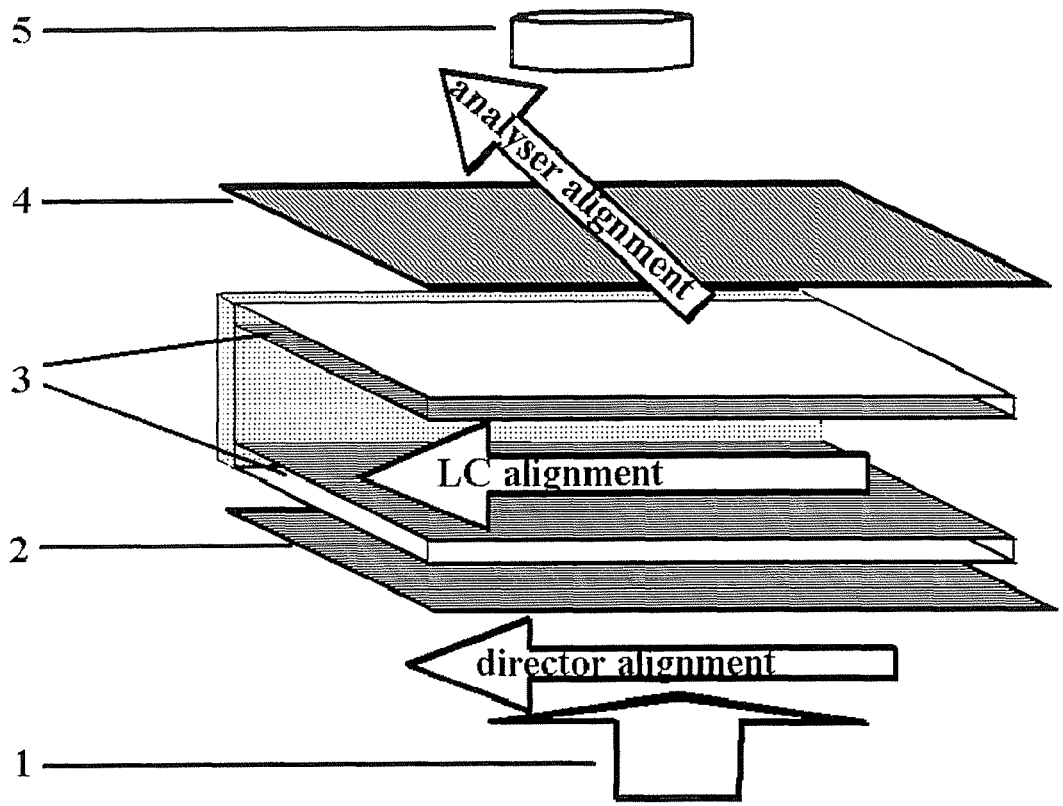
FIG. 9 is a schematic representation of the arrangement of the detection chamber, polarizers, light source and light detector in the assay cassette setup.

A schematic of the detection chamber, polarizing filters, light source and detector is shown in FIG. 9. The setup consists of a light source (designated as "1" in FIG. 9), an initial polarizer called the director (designated as "2" in FIG. 9), the detection chamber (designated as "3" in FIG. 9) the secondary polarizer called the analyzer (designated as "4" in FIG. 9) and the light detector (designated as "5" in FIG. 9). As described earlier, the first, or director, polarizer is aligned such that light passing through the polarizer is aligned with the longitudinal axis of the detection chamber (i.e., along the "easy axis"), parallel to the microgrooves of the detection chamber, and in the same direction as flow of fluid into the detection chamber. The second, or analyzer, polarizer is aligned perpendicular or 90° to the first polarizer. So configured, the two polarizers are said to be "crossed."

In operation, the detection chamber contains the mixed sample (sample mixed with receptor, optional microspheres, and liquid crystalline material). In one instance, the mixed sample, containing the liquid crystalline material, does not contain complexes between ligands and receptors. In a second instance, the mixed sample containing the liquid crystalline material does contain complexes between ligands and receptors.

In the situation where there are no complexes, a stream of light from the light source contacts the first, director polarizer. The light that emerges or passes through the polarizer is linearly polarized in the direction of the microgrooves in the detection chamber. The polarized light then is transmitted through the ordered liquid crystal in the detection chamber. The transmitted light then contacts the second, analyzer polarizer. Because there were no ligand-receptor complexes present in the liquid crystal, the liquid crystal orientation is not disrupted and thus light cannot be transmitted through the liquid crystal. The light emerging from the liquid crystal in the detection chamber is, therefore, unable to pass through the second, analyzer light polarizer which is 90° to the director. Since no light passes through the second polarizer, there is no light contacting the light detector of the system.

Figure 13:
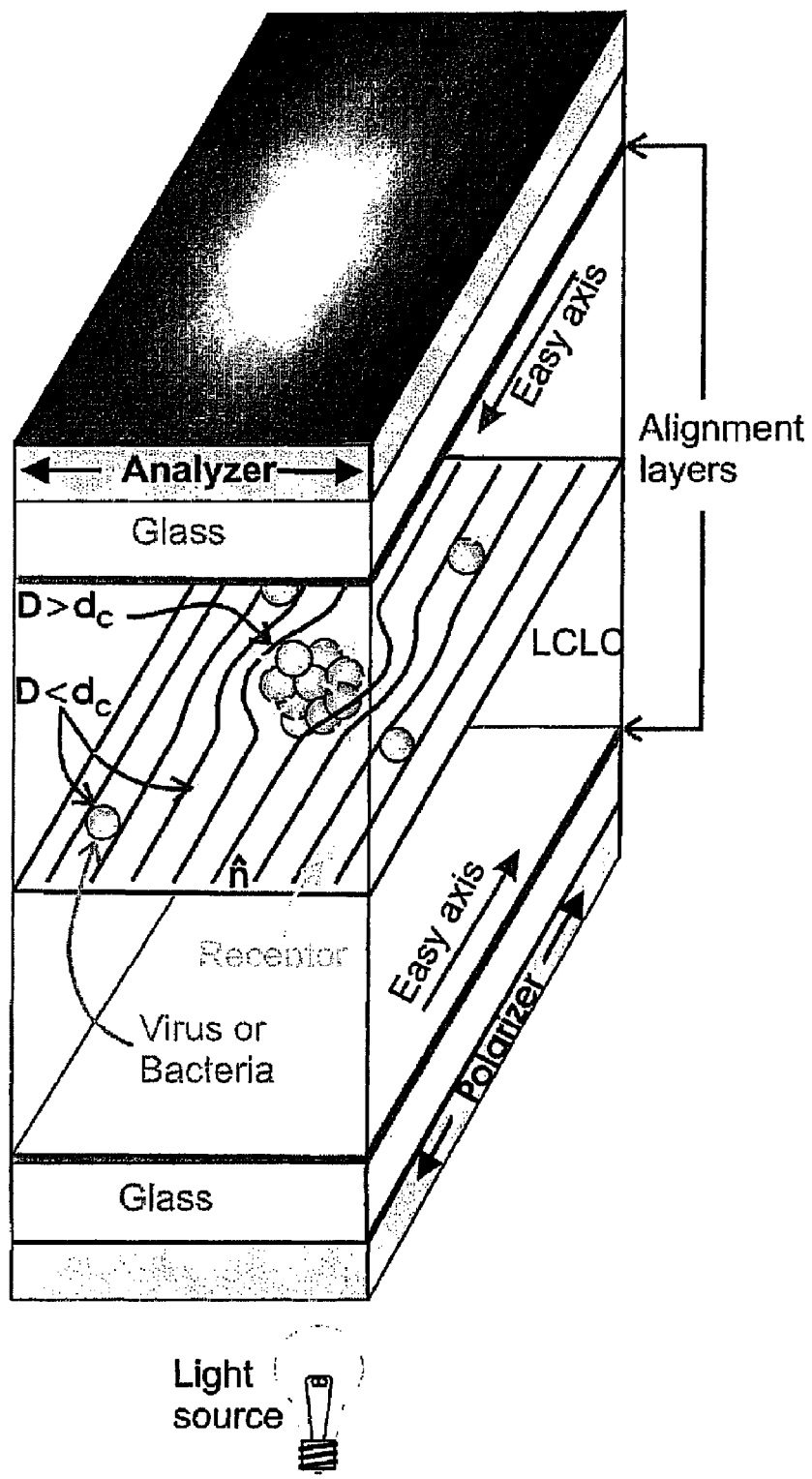
FIG. 13 is a schematic representation of detection of aggregates in a detection chamber.

In the situation where there are complexes between ligand and receptor present in the liquid crystal mixture, the result is different (see FIG. 13). In that case, a stream of light from the light source also contacts the first polarizer. The light emerging from the first polarizer is polarized in the direction of the microgrooves in the detection chamber, as in the first example. However, when the linearly polarized light contacts the distorted liquid crystal surrounding the complexes within the detection chamber, at least some of the light is transmitted. The complexes, which contain ligand bound to receptor (e.g., an antigen-antibody complex), or a ligand-receptor complex bound by one or more microspheres, causes a local distortion in the orientational order of the liquid crystal in the vicinity of the complex. The presence of these distortions of the liquid crystal permits transmission of light. This transmitted, extra-ordinary, light passes through the second polarizer. The light crossing the second polarizer contacts the light detector and is measured as a light signal. The light signal indicates presence of ligands in the sample that were bound by the specific receptor. The light signal can be quantified and can be correlated with the concentration of ligands in the sample.

In the system described above, the size of the aggregate (i.e., ligand plus receptor) is preferably at least 2 $\mu$m in diameter in order to provide for light transmission through the detection chamber. Generally, ligands of approximately 1 $\mu$m in diameter, when bound with an antibody receptor provides for an aggregate in the range of 2 $\mu$m in diameter. Preferably, however, microspheres of up to approximately 1 $\mu$m in diameter, which are capable of binding to the receptors, are also provided. Ligands and receptors complex to form aggregates and the resulting aggregates distort the orientational order of a liquid crystal. Addition of such microspheres increases the sensitivity of the system by increasing the size of the aggregates and causing increased distortion of the liquid crystal. For example, in the case where such microspheres are used, a ligand of approximately 1 $\mu$m in diameter binds to antibody receptors and produces a complex or aggregate of approximately 2 $\mu$m in diameter. One or more microspheres, each approximately 1 $\mu$m in diameter, then binds to the receptors bound to the ligand. When this occurs a complex of even larger size is produced. Such larger complexes amplify transmission of polarized light through the liquid crystal.

The system described above using a detection chamber of the approximate dimensions as shown in FIG. 8, provides for detection of approximately $10^4$ ligands per ml of initial sample. Concentration of the initial sample is able to provide more sensitivity of the system.

Sample Collection and Preprocessing

The sample which is introduced into the assay cassette is collected from the environment or is collected from a human or animal subject. The sample is either a dry, non-liquid sample or a liquid sample. If the sample is not liquid, or if the sample is liquid but in a small volume (e.g., less than 0.1 ml), in one embodiment the volume of the sample is increased to at least 0.2 ml by addition of sterile water or other biological buffer.

The sample is then treated to remove any material of an approximate size larger than 1 $\mu$m in diameter. Particles of a size larger than this can cause distortion of the liquid crystal in the absence of receptor binding to ligand. This increases background signal and decreases sensitivity of the system.

There are a variety of methods for removing material larger than 1 $\mu$m from the sample. In one method, the sample is centrifuged at a force that is not large enough to cause microorganisms or other ligands (e.g., of around 1-2 $\mu$m in diameter) to be removed from solution, but is large enough to cause material larger than 2 $\mu$m in diameter to be removed. Alternatively, the sample is passed through a prefilter having a pore size of larger than approximately 1 $\mu$m. The sample, which has been either centrifuged or passed through a prefilter, is then passed through a filter having a pore size of less than 2 $\mu$m. Matter larger than the pore size is trapped on the filter. The material trapped on the filter is discarded.

Figure 12:
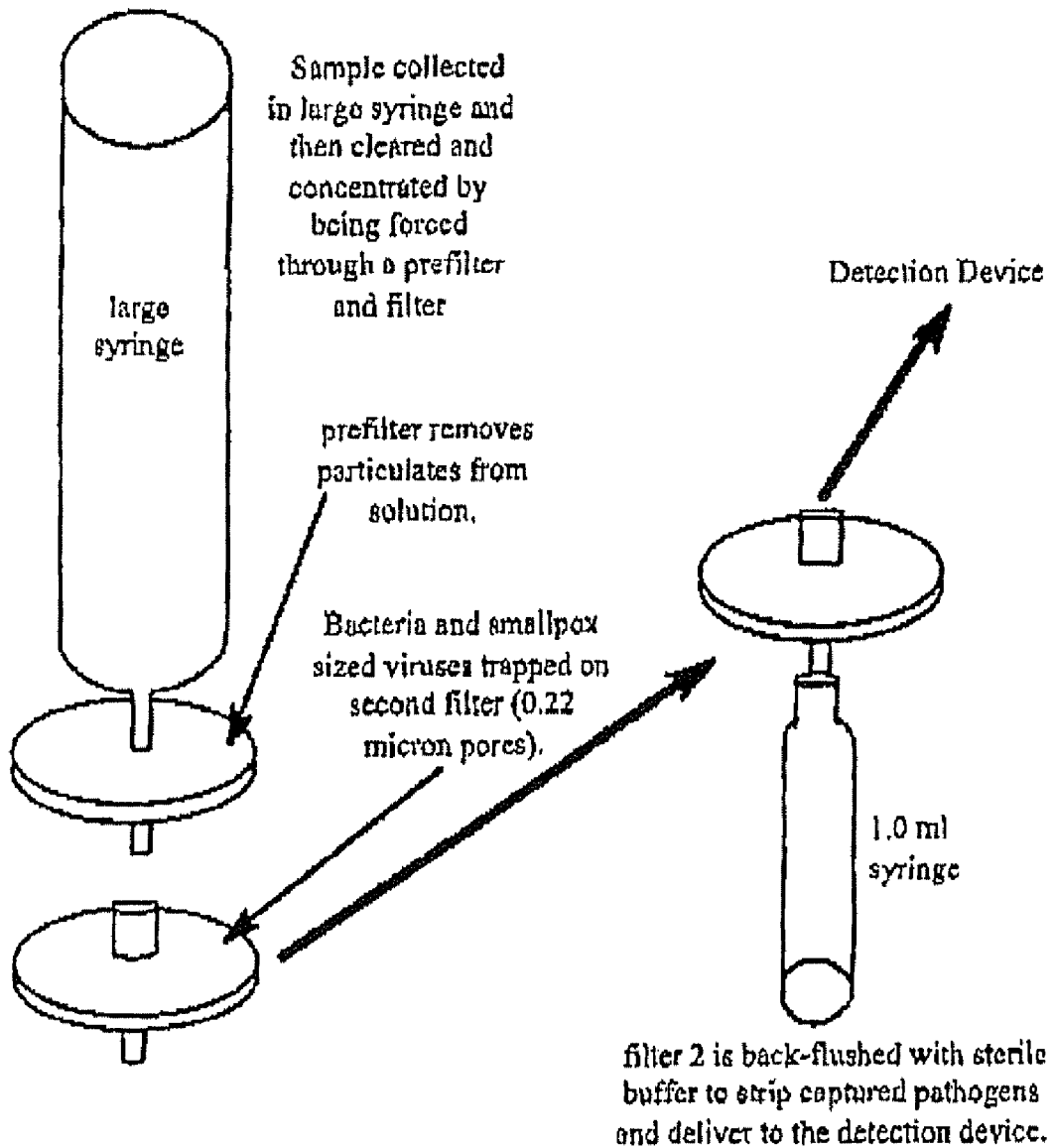
FIG. 12 is a schematic representation of a filtration system for removing particulate material from a sample before it is introduced into the assay cassette.

An example of a device that can be used for this purpose is shown in FIG. 12. The sample is first passed through a large pore filter (1.5 $\mu$m pores) to remove large particulates and then passed through a second filter device (0.22 $\mu$m pore size) to remove excess volume). As is shown in FIG. 12, the ligand that is to be introduced into the assay cassette is trapped on the second filter and then removed from the filter by back-flushing the filter with a smaller than original volume. The resulting fully-treated, concentrated sample is then introduced into the assay cassette to determine the presence of specific ligands therein.

Other methods for preprocessing the sample before introduction into the cassette can be used.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

While particular embodiments of the subject invention have been described, it will be obvious to those skilled in the art that various changes and modifications of the subject invention can be made without departing from the spirit and scope of the invention. In addition, while the present invention has been described in connection with certain specific embodiments thereof, it is to be understood that this is by way of illustration and not by way of limitation and the scope of the invention is defined by the appended claims which should be construed as broadly as the prior art will permit.

EXAMPLES

The invention may be better understood by reference to the following examples, which serve to illustrate but not to limit the present invention.

Example 1

Making a Detection Chamber

Biosensor assays were conducted in chambers created by using mylar (20 µm) spacers to separate two parallel glass slides (25 mm). Before chamber assembly, the optical quality glass (Fisher Scientific, Pittsburgh, Pa.) slides were cleaned (sonicated in 1% Alconox in distilled water for 10 min at 60° C.), air dried in a clean room, and spin coated at 1500 rpm with 3% v/v polyimide SE-7511 (Nissan Chemical, Japan). The slides were dried at 100° C. for 2 min and baked at 180° C. for 1 hr to form a polyimide film (≈380 nm thick) on one surface. The treated surface was rubbed with felt (⅛ inch felt; 10 in/sec; 0.12 lb/in$^2$) to create parallel microgrooves in the polyimide. The direction of the microgrooves functions to uniformly align the liquid crystal in the chamber. Assay chambers were constructed by sandwiching a mixed sample between two slides that were coated, rubbed and aligned in an anti-parallel fashion. The distance between the slides was fixed with mylar (3M, St. Paul, Minn.) spacers (20 µm) located at the cassette edges. When filled, the chambers were sealed with epoxy.

Example 2

Creating Artificial Aggregates

The model ligand used was a fluorescent-labeled (Dragon Green fluor), antigen coated (streptavidin) latex bead (Bangs Laboratories, Inc., Fishers, Ind.). The size of an individual bead was 0.56 µm Anti-streptavidin antibody (1.0 µg/ml; Rochland, Inc., Gilbertsville, Pa.) was mixed with the streptavidin-coated beads to create immune aggregates that would cause birefringence. Experimentally, beads, antibody or immune aggregates were added to liquid crystal to create a final LCLC concentration of 13% cromolyn (CAS#: 15826-37-6; Spectrum Chemical Mfg. Corp.; Gardena, Calif.) in deionized water (w/w). The stock solution of cromolyn was filtered (0.2 µm) to remove undissolved particles and impurities. The 13% cromolyn had a thermal stability, as measured by Differential Scanning Calorimetry (Perkin Elmer DSC7, Shelton, Conn.) between 2° C. and 22° C.

Example 3

Analysis of Aggregates

Sample filled cassettes were evaluated using a confocal microscope (Olympus Flowview; Ar laser excitation at 488 nm; power <1 µW; 40× objective had a NA=0.6; pinhole aperture=100 µm). Fluorescent light from the focal plane in the LCLC cassette passed through the pinhole and was divided and directed into two different detection channels by the beam splitter. The 3-dimensional location of the fluorescently labeled bead was detected by a photo-multiplier tube. The image was simultaneously evaluated by transmission-mode polarizing microscopy (PM) to measure the intensity of light $I_{PM}$ that passed through the polarizer (P), LCLC cassette, and analyzer (A). Simultaneous confocal and polarizing microscopy allowed correlation of the immune aggregates with the associated director distortions in the surrounding LCLC.

Experimentally, the polarizer was aligned along the easy axis of the LC in the cassette. The analyzer was then oriented perpendicular (+90°) to the polarizer and light was applied. The data shown in FIGS. 14 and 15 demonstrate that inclusion bodies must exceed a critical diameter (see below) before distortion of the LCLC is sufficient to permit detectable transmission of light.

Figure 14:
FIG. 14 shows the effect of immune complex size on director distortions in the surrounding LCLC. Left column contains fluorescence confocal microscopy textures and the right column contains the corresponding polarizing microscope textures. Small aggregates (A) with $d<d_c$, where $d_c \approx 2$ μm, did not cause director distortions (B). Aggregates of size $d \approx d_c$ (C) gave rise to minimally detectable distortions (D). Aggregates exceeding the critical radius, $d>d_c$, (E) caused substantial director distortions readily visualized by polarizing microscopy (F).

As shown in FIG. 14, immune complexes observed in the confocal mode were detected by fluorescent markers (A, C and E). The polarizing-mode textures of the same regions (B, D and F) depended on the size of complexes. Complexes (as well as individual non-reacted beads and antibodies) smaller than 2 microns in diameter did not cause noticeable light transmission through the crossed polarizers and the LCLC sample, $I_{PM}$≈0. In contrast, complexes larger than 2 microns produced noticeable light transmission caused by director distortions in the surrounding LCLC matrix. Note that the director distortions caused by immune complexes of size d>$d_c$, are much larger than d (compare and F). In control samples, non-reacted antibodies and antigens did not cause noticeable light transmittance in polarizing-microscope observations.

Figure 15:
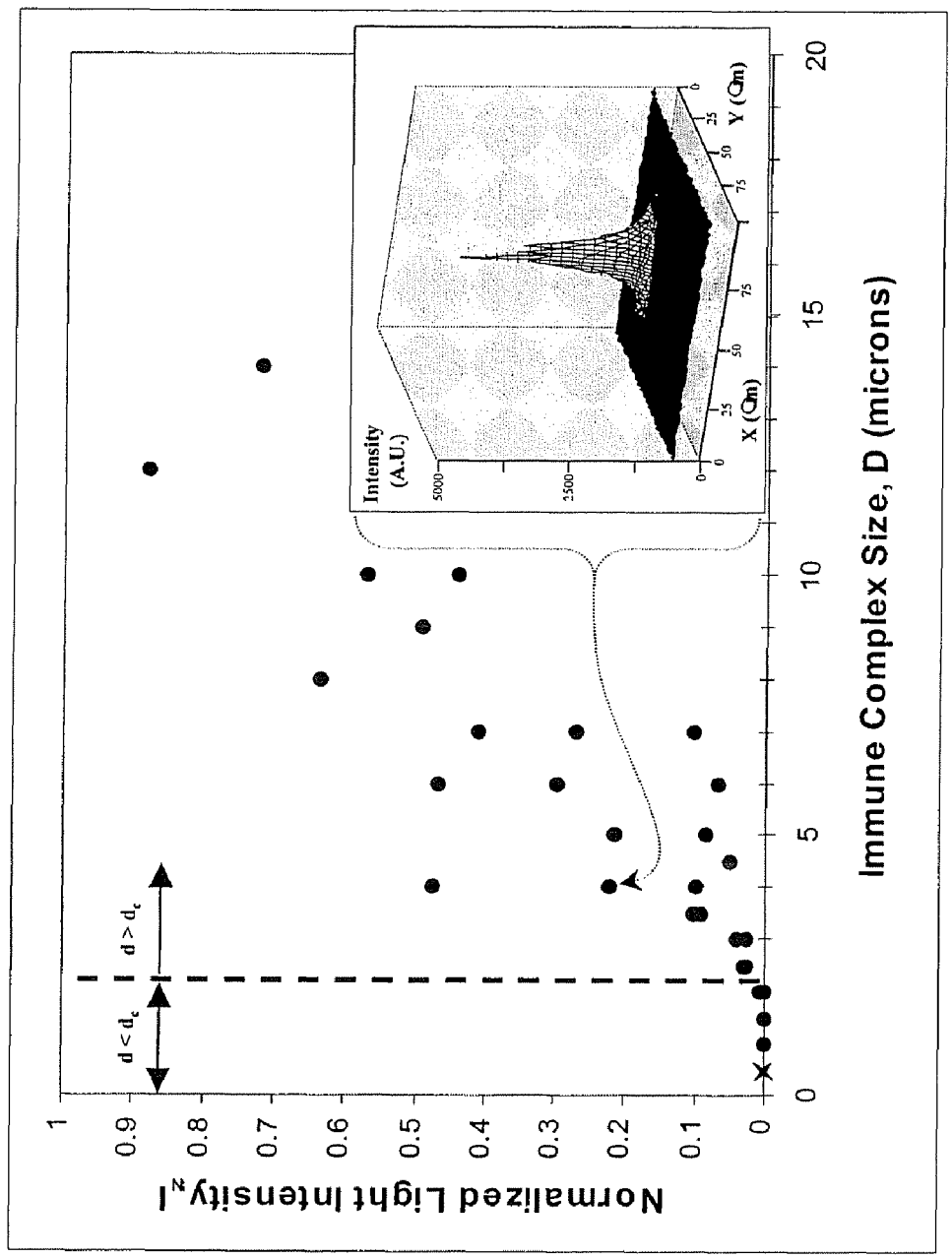
FIG. 15 shows normalized light transmission, $I_N$ through a 15 μm thick LCLC sample in the polarizing-microscope mode as the function of size (average diameter) of the immune complex. The inset shows the signal intensity created by a ~4 μm diameter aggregate in a 50 μm×50 μm area of LCLC. The signal amplitude (insert) is an order of magnitude higher than the background.

FIG. 15 shows that the intensity of transmitted light increased with the size of complexes once the complexes become larger than $d_c$≈2 µm. Complexes (or individual beads) of size d<$d_c$ did not influence the background transmission (which is always present because of the static and dynamic fluctuations of the LCLC director). Each data point represents an immune complex that was first detected and characterized by fluorescence microscopy. The (average) complex diameter was measured using an eyepiece micrometer. Then the polarizing-microscope mode was used to measure and normalize the intensity of light passing through a 50 µm×50 µm area of LCLC cassette with the identified complex at the center of it. The normalized light intensity $I_N$ was determined by the formula $$I_N = \frac{I_t - I_b}{I_b - I_b},$$

where $I_t$ is the light intensity transmitted through the 50 µm×50 µm area with the director distortions caused by the complex, $I_b$ is light intensity transmitted through the 50 µm×50 µm area of an unperturbed (uniform) part of the same sample, and $\bar{I}_b$ is the transmittance through the same uniform area rotated by 5° with respect to the polarizer. The quantity $I_N$ is normalized by the uniform bright field and reflects the relative amplitude (angle β) of director distortions.

It should be noted that the threshold-like feature of transmittance vs. size dependence allows tuning of the detection system when a variety of parameters change (cassette thickness, alignment layer, type of LCLC or the microbes, value of $d_c$, etc.).

Example 4

Detection of Bacterial and Viral Immune Aggregates

The biosensor system was tested against bacteria (*Escherichia coli* k99, # 31616) and against virus (Vaccinia virus, VR-1354) obtained from the American Type Culture Collection, Herndon, Va. The activity and specificity of commercially available anti-*E. coli* monoclonal antibody (K99, Denka-Seiken; Tokyo, Japan) and anti-vaccinia polyclonal antibody (ANAWA Biomedical Services & Products; Tokyo, Japan) were confirmed in the laboratory before use.

For the bacterial study, *E. coli* was grown (37° C.) to late log phase in nutrient broth (Becton Dickinson, Sparks, Md.), washed twice with sterile phosphate-buffered saline (pH 7.2, PBS) and resuspended in PBS ($10^8$ bacteria/ml). Bacteria ($2 \times 10^6$ *E. coli*) were added to 20 ng of anti-*E. coli* antibody, gently mixed, added to LCLC (12% final cromolyn concentration) and incubated for two minutes at room temperature. PBS was substituted for bacteria or antibody in control reactions. Cassettes were assembled using 8 µm Mylar spacers and viewed by polarizing microscopy as described earlier.

Figure 16:
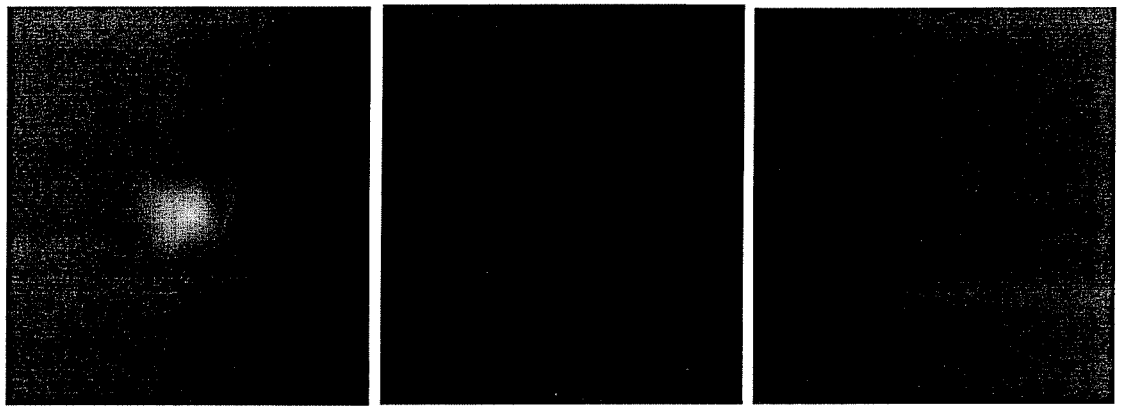
FIG. 16 shows detection of Bacteria-Antibody Complexes. Polarizing micrographs of LCLC with added *E. coli* and antibody (A); *E. coli* only (B); antibody only (C). An immune aggregate was associated with the area of light transmission in (A).

The results showed that the aggregated E. Coli distorted the surrounding LCLC to produce detectable birefringent spots (FIG. 16A), as compared with non-aggregated bacterial or antibody control (FIGS. 16B and 16C).

Figure 17:
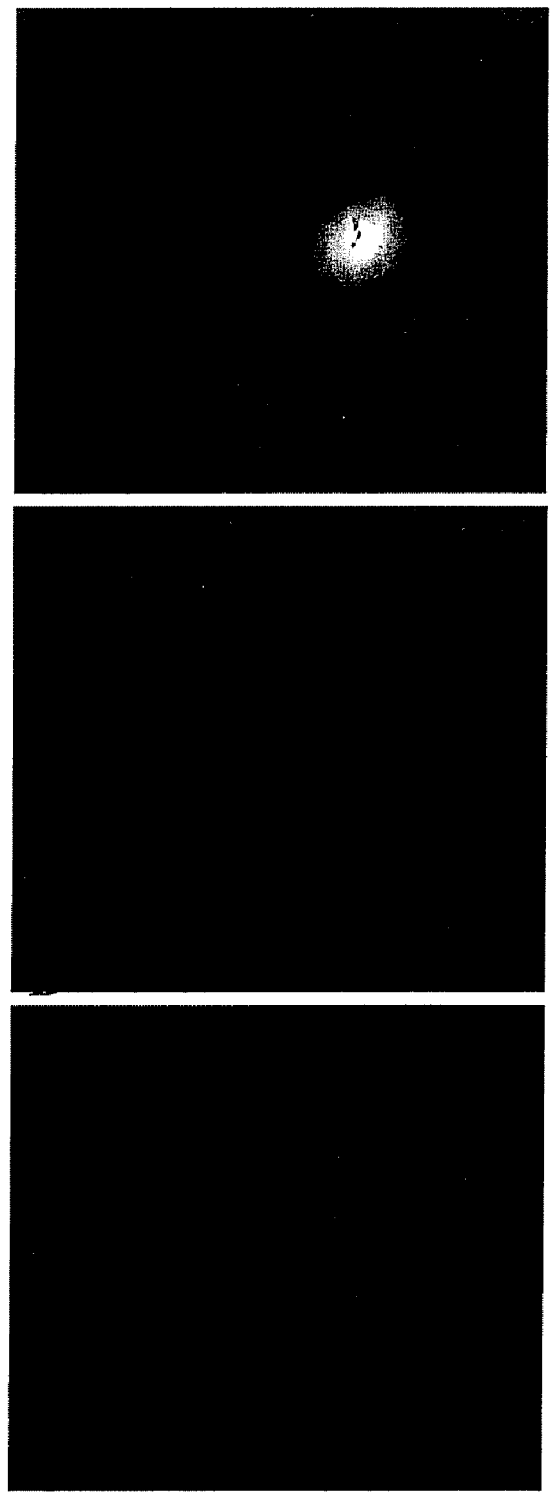
FIG. 17 shows detection of Virus-Antibody Complexes. Polarizing micrographs of Vaccinia virus with antibody (A), Vaccinia only (B), and antibody only (C) in 13% (w/w) cromolyn. Note the elongated immune aggregate of Vaccinia virus and associated light transmission in (A).

Similar birefringent areas formed around viral immune aggregates ($1.8 \times 10^3$ virions plus 20 ng antibody) embedded in 13% cromolyn (FIG. 17A). Neither individual virions (FIG. 17A) nor antibody (FIG. 17B) caused birefringence in the 13% cromolyn. The lyotropic chromonic liquid crystal functioned as an effective and rapid biosensor.

What is claimed is:

1. A flow channel module for use in a device for detecting the presence of a ligand in a sample, comprising:
    a first chamber comprising in its interior a composition which exhibits specificity for a ligand, wherein the composition comprises at least one member selected from the group consisting of a microparticle and a receptor;
    a second chamber comprising in its interior a liquid crystalline material;
    a detection chamber delineated on at least two opposing sides by a low or non birefringent transparent plate, wherein one or more surfaces of the low or non birefringent plate has longitudinal microgrooves oriented along an axis that is parallel to the direction of flow into the detection chamber; and
    an inlet port;
    wherein the first chamber, the second chamber, and the detection chamber are arranged in series, and wherein the inlet port is in fluid communication with the first chamber, the first chamber is in fluid communication with the second chamber, and the second chamber is in fluid communication with the detection chamber.

2. The flow channel module according to claim 1, wherein the first chamber comprises in its interior a microparticle and a receptor which exhibits specificity for a ligand, and wherein a sample ligand, the receptor, the microparticle, and the liquid crystalline material are mixed and the sample ligand is bound to the receptor prior to entering the detection chamber such that the detection chamber receives the sample ligand bound to the receptor mixed with the liquid crystalline material to permit detection of a receptor-ligand complex.

3. The flow channel module according to claim 1, wherein the first chamber comprises in its interior a microparticle and a receptor which exhibits specificity for a ligand, and wherein a sample ligand, the receptor, the microparticle, and the liquid crystalline material are mixed prior to entering the detection chamber and alignment of the liquid crystalline material into an ordered liquid crystal matrix within the detection chamber permits exhibition of the specificity of the receptor for the sample ligand.

4. The flow channel module according to claim 1, comprising a first conduit between the first chamber and the second chamber and a second conduit between the second chamber and the inlet of the detection chamber.

5. The flow channel module according to claim 4, wherein one or both of the first conduit and the second conduit comprise structures that induce turbulent flow when the device is in use.

6. The flow channel module according to claim 5, wherein the structures that induce turbulent flow are selected from the group consisting of baffles, blades, ribs, bars and combinations thereof.

7. The flow channel module according to claim 6, wherein the structures that induce turbulent flow are either moving or non-moving.

8. The flow channel module according to claim 1, wherein laminar flow is induced prior to the detection chamber when the device is in use.

9. The flow channel module according to claim 3 further comprising conduits between all or any of the inlet port, the first chamber, the second chamber, and the detection chamber that comprise structures that induce turbulent flow when the device is in use.

10. A flow channel module for use in a device for detecting the presence of a ligand in a sample, comprising:
    a first chamber comprising in its interior a receptor which exhibits specificity for a ligand;
    a second chamber comprising in its interior a liquid crystalline material; and
    a detection chamber that is in fluid communication with said first and second chambers;
    wherein a sample ligand, the receptor, and the liquid crystalline material are mixed and the sample ligand is bound to the receptor prior to entering the detection chamber; and
    wherein the detection chamber permits the mixture of the sample ligand, the receptor, and the liquid crystalline material to form an ordered liquid crystal matrix to permit detection of a receptor-ligand complex.

11. The flow channel module of claim 10, wherein the chambers are arranged in series, and wherein an inlet port is in fluid communication with the first chamber, the first chamber is in fluid communication with the second chamber, and the second chamber is in fluid communication with the detection chamber.

12. The flow channel module of claim 11, wherein conduits between all or any of the first chamber, the second chamber, and the detection chamber comprise structures that induce turbulent flow when the device is in use.

13. A flow channel module for use in a device for detecting the presence of a ligand in a sample, comprising:
- a first chamber comprising in its interior a receptor which exhibits specificity for a ligand and a microparticle which exhibits specificity for the receptor;
- a second chamber comprising in its interior a liquid crystalline material; and
- a detection chamber;
- wherein a sample ligand, the receptor, the microparticle, and the liquid crystalline material are mixed and the sample ligand is bound to the receptor prior to entering the detection chamber; and
- wherein the detection chamber permits the mixture of the sample ligand, the receptor, the microparticle, and the liquid crystalline material to form an ordered liquid crystal matrix to permit detection of a receptor-ligand complex; and
- wherein the chambers are arranged in series with the first chamber in fluid communication with the second chamber and the second chamber in fluid communication with the detection chamber.

14. The flow channel of claim 13, wherein the receptor is an antibody.

15. The flow channel module of claim 13, wherein the detection chamber is delineated on at least two opposing sides by a low or non birefringent transparent plate, wherein one or more surfaces of the low or non birefringent plate has longitudinal microgrooves oriented along an axis that is parallel to the direction of flow into the detection chamber.

16. The flow channel module of claim 15 further comprising an inlet port that is in fluid communication with the first chamber.

17. The flow channel module of claim 15 further comprising conduits between each of said chambers.

18. The flow channel module of claim 17, wherein the conduit between the first and second chambers comprises structures that induce turbulent flow when the device is in use.

19. A flow channel module for use in a device for detecting the presence of a ligand in a sample, comprising:
- an inlet port;
- a mixing chamber in fluid communication with the inlet port, the mixing chamber comprising in its interior a receptor which exhibits specificity for a ligand, a microparticle which exhibits specificity for the receptor, and a liquid crystalline material; and
- a detection chamber in fluid communication with the mixing chamber;
- wherein a sample ligand, the receptor, the microparticle, and the liquid crystalline material are mixed and the sample ligand is bound to the receptor prior to entering the detection chamber; and
- wherein the detection chamber permits the mixture of the sample ligand, the receptor, the microparticle, and the liquid crystalline material to form an ordered liquid crystal matrix to permit detection of a receptor-ligand complex.

20. The flow channel module of claim 19, wherein the detection chamber is delineated on at least two opposing sides by a low or non birefringent transparent plate, and wherein one or more surfaces of the low or non birefringent plate has longitudinal microgrooves oriented along an axis that is parallel to the direction of flow into the detection chamber.

21. The flow channel module of claim 19, wherein laminar flow of the mixture of the sample ligand, the receptor, the microparticle, and the liquid crystalline material is induced prior to entering the detection chamber when the device is in use.

* * * * *

UNITED STATES PATENT AND TRADEMARK OFFICE
CERTIFICATE OF CORRECTION

| | | |
|---|---|---|
| PATENT NO. | : 7,811,811 B2 | Page 1 of 1 |
| APPLICATION NO. | : 11/422828 | |
| DATED | : October 12, 2010 | |
| INVENTOR(S) | : Gary D. Niehaus | |

It is certified that error appears in the above-identified patent and that said Letters Patent is hereby corrected as shown below:

Claim 4, Column 22, line 24, after the word "and" delete the words "the inlet of".

Signed and Sealed this

Twenty-first Day of December, 2010

David J. Kappos
*Director of the United States Patent and Trademark Office*